(12) United States Patent
Olek et al.

(10) Patent No.: US 7,229,759 B2
(45) Date of Patent: Jun. 12, 2007

(54) HIGHLY SENSITIVE METHOD FOR THE DETECTION OF CYTOSINE METHYLATION PATTERNS

(75) Inventors: Alexander Olek, Berlin (DE); Kurt Berlin, Stahnsdorf (DE)

(73) Assignee: Epigenomics AG, Berlin (DE)

( * ) Notice: Subject to any disclaimer, the term of this patent is extended or adjusted under 35 U.S.C. 154(b) by 512 days.

(21) Appl. No.: 10/229,370

(22) Filed: Aug. 27, 2002

(65) Prior Publication Data

US 2003/0082600 A1 May 1, 2003

Related U.S. Application Data

(63) Continuation-in-part of application No. PCT/EP02/02572, filed on Mar. 8, 2002.

(30) Foreign Application Priority Data

Mar. 9, 2001 (DE) ............... 101 12 515
Nov. 19, 2001 (DE) ............... 101 58 283

(51) Int. Cl.
*C12Q 1/68* (2006.01)
*C12N 15/11* (2006.01)

(52) U.S. Cl. .................... 435/6; 536/24.33
(58) Field of Classification Search ............ 435/6, 435/91.2
See application file for complete search history.

(56) References Cited

U.S. PATENT DOCUMENTS

| | | | |
|---|---|---|---|
| 5,849,497 A | 12/1998 | Steinman | 435/6 |
| 5,952,202 A | 9/1999 | Aoyagi et al. | 435/91.2 |
| 6,331,393 B1 * | 12/2001 | Laird et al. | 435/6 |

FOREIGN PATENT DOCUMENTS

WO WO 99/55905 A1 * 11/1999

OTHER PUBLICATIONS

Herman et al, Proc. Natl. Acad. Sci. USA. 93: 9821 (1996).*
Kashiwabara et al, Int. J. Cancer (Pred. Oncol.) 79: 215 (1998).*
Orum et al, Nucleic Acids Res. 21: 5332 (1993).*
Yu et al, BioTechniques 23: 714 (1997).*
Molecular Biology Reagents/Protocols 1992, United States Biochemical Corporation, 1991, Cleveland, Ohio, pp. 218-219.*
International Preliminary Examimation Report for PCT Application No. PCT/EP02/02572 (the present application being a CIP of said PCT application).
International Search Report for PCT Application No. PCT/EP02/02572 (the present application being a CIP of said PCT application) mailed Mar. 21, 2003.
Gonzalgo et al., Nucleic Acids Research, 25(12):2529-31 (1997).

* cited by examiner

*Primary Examiner*—James Martinell
(74) *Attorney, Agent, or Firm*—Kriegsman & Kriegsman

(57) ABSTRACT

The present invention concerns a method for the detection of cytosine methylation in DNA samples, wherein the following steps are conducted: (a) a genomic DNA sample, which comprises the DNA to be investigated and background DNA, is chemically treated in such a way that all of the unmethylated cytosine bases are converted to uracil, whereas the 5-methylcytosine bases remain unchanged; (b) the chemically treated DNA sample is amplified with the use of at least 1 primer oligonucleotide as well as a polymerase, whereby the DNA to be investigated is preferred as the template over the background DNA, and (c) the amplified products are analyzed and the methylation status in the DNA to be investigated is concluded from the presence of an amplified product and/or from the analysis of additional positions.

39 Claims, 15 Drawing Sheets

DNA 1 (SEQ ID NO:30)

TCGTCGTCGTAGTTTTCGTTATTAGTGAGTACGCGCGGTTCGCGTTTTCGGGGATGGGGTTTAGAG

DNA 2 (SEQ ID NO:31)

TTGTTGTTGTAGTTTTTGTTATTAGTGAGTATGTGTGGTTTGTGTTTTTGGGGATGGGGTTTAGAG

B)

PRIMER ATCACTCATGCGCGC (SEQ ID NO:32)

T*CGTCGTCG*TAGTTTTCGTTATTAGTGAGTA*CGCGCG*GTT*CGCGT*TTT*C*GGGGATGGGGTTTAGAG
(SEQ ID NO:30)

PRIMER ATCACTCATGCGCGC (SEQ ID NO:32)

T*TGTTGT*TGTAGTTTT*T*GTTATTAGTGAGTA*TGTGTG*GTT*TGTGT*TTT*T*GGGGATGGGGTTTAGAG
(SEQ ID NO:31)

C)
        PRIMER ATCACTCATRCRCRC (SEQ ID NO:33)

T*CGTCGTCG*TAGTTTTCGTTATTAGTGAGTA*CGCGCG*GTT*CGCGT*TTT*C*GGGGATGGGGTTTAGAG
(SEQ ID NO:30)

PRIMER ATCACTCATRCRCRC (SEQ ID NO:33)

T*TGTTGT*TGTAGTTTT*T*GTTATTAGTGAGTA*TGTGTG*GTT*TGTGT*TTT*T*GGGGATGGGGTTTAGAG
(SEQ ID NO:31)

D)
        PRIMER ATCACTCATICICIC (SEQ ID NO:34)

T*CGTCGTCG*TAGTTTTCGTTATTAGTGAGTA*CGCGCG*GTT*CGCGT*TTT*C*GGGGATGGGGTTTAGAG
(SEQ ID NO:30)

PRIMER ATCACTCATICICIC (SEQ ID NO:34)

T*TGTTGT*TGTAGTTTT*T*GTTATTAGTGAGTA*TGTGTG*GTT*TGTGT*TTT*T*GGGGATGGGGTTTAGAG
(SEQ ID NO:31)

Fig. 7

A)
```
      PRIMER       AATAATCACTCAT (SEQ ID NO:35)
                                      ACACACCAAACACAAA BLOCKER (SEQ ID NO:36)
TCGTCGTCGTAGTTTTCGTTATTAGTGAGTACGCGCGGTTCGCGTTTTCGGGGATGGGGTTTAGAG
(SEQ ID NO:30)

PRIMER       AATAATCACTCAT (SEQ ID NO:35)
                                      ACACACCAAACACAAA BLOCKER (SEQ ID NO:36)
TTGTTGTTGTAGTTTTTGTTATTAGTGAGTATGTGTGGTTTGTGTTTTGGGGATGGGGTTTAGAG
(SEQ ID NO:31)
```

B)
```
      PRIMER       AATAATCACTCAT (SEQ ID NO:35)
                          AGTGAGTAACACACCAA       BLOCKER (SEQ ID NO:37)
TCGTCGTCGTAGTTTTCGTTATTAGTGAGTACGCGCGGTTCGCGTTTTCGGGGATGGGGTTTAGAG
(SEQ ID NO:30)

PRIMER       AATAATCACTCAT (SEQ ID NO:35)
                          AGTGAGTAACACACCAA       BLOCKER (SEQ ID NO:37)
TTGTTGTTGTAGTTTTTGTTATTAGTGAGTATGTGTGGTTTGTGTTTTGGGGATGGGGTTTAGAG
(SEQ ID NO:31)
```

C)
```
            PRIMER ATCACTCATRCRCRC (SEQ ID NO:33)
                      ATCACTCATAGAGAGCAA      BLOCKER (SEQ ID NO:38)
TCGTCGTCGTAGTTTTCGTTATTAGTGAGTACGCGCGGTTCGCGTTTTCGGGGATGGGGTTTAGAG
(SEQ ID NO:30)

PRIMER ATCACTCATRCRCRC (SEQ ID NO:33)
                      ATCACTCATAGAGAGCAA      BLOCKER (SEQ ID NO:38)
TTGTTGTTGTAGTTTTTGTTATTAGTGAGTATGTGTGGTTTGTGTTTTGGGGATGGGGTTTAGAG
(SEQ ID NO:31)
```

D)
```
            PRIMER ATCACTCATRCRCRCCAA (SEQ ID NO:39)
          (SEQ ID NO:40) ACACACCAAACACAAAAA      BLOCKER
TCGTCGTCGTAGTTTTCGTTATTAGTGAGTACGCGCGGTTCGCGTTTTCGGGGATGGGGTTTAGAG
(SEQ ID NO:30)

PRIMER ATCACTCATRCRCRCCAA (SEQ ID NO:39)
          (SEQ ID NO:41) ACACACCAAACACAAAAAC     BLOCKER
TTGTTGTTGTAGTTTTTGTTATTAGTGAGTATGTGTGGTTTGTGTTTTGGGGATGGGGTTTAGAG
(SEQ ID NO:31)
```

Fig. 8

```
PRIMER1 AATAATCACTCAT (SEQ ID NO:35)
                                    ACACCAAACACAAA BLOCKER (SEQ ID NO:42)
TCGTCGTCGTAGTTTTCGTTATTAGTGAGTACGCGCGGTTCGCGTTTTCGGGGATGGGGTTTAGAG
(SEQ ID NO:30)
                         PRIMER 2         CCCCTACCCCAAA
                                          (SEQ ID NO:43)

PRIMER1 AATAATCACTCAT (SEQ ID NO:35)
                                    ACACCAAACACAAA BLOCKER (SEQ ID NO:42)
TTGTTGTTGTAGTTTTTGTTATTAGTGAGTATGTGTGGTTTGTGTTTTTGGGGATGGGGTTTAGAG
(SEQ ID NO:31)
                         PRIMER 2         CCCCTACCCCAAA
                                          (SEQ ID NO:43)
```

Fig. 9

A (SEQ ID NO:44)
GTTTTTGTTATTAGTGAGTATGTGTGGTTTGTGTTTTTGGGGATGGGGTTTAGAG
TTTTAGTATGGGGTTAATTTGTAGTATTAGGTTTGGGTTTTTGGTAGGGTTTTTT
TTTATTTTGAGATTTGGGATGGGGGTTTAGGGGATTTAGGA

B (SEQ ID NO:45)
GTTTTCGTTATTAGTGAGTACGCGCGGTTCGCGTTTTCGGGGATGGGGTTTAGAG
TTTTAGTATGGGGTTAATTCGTAGTATTAGGTTCGGGTTTTCGGTAGGGTTTTTC
TTTATTTCGAGATTCGGGACGGGGGTTTAGGGGATTTAGGA

Fig. 10
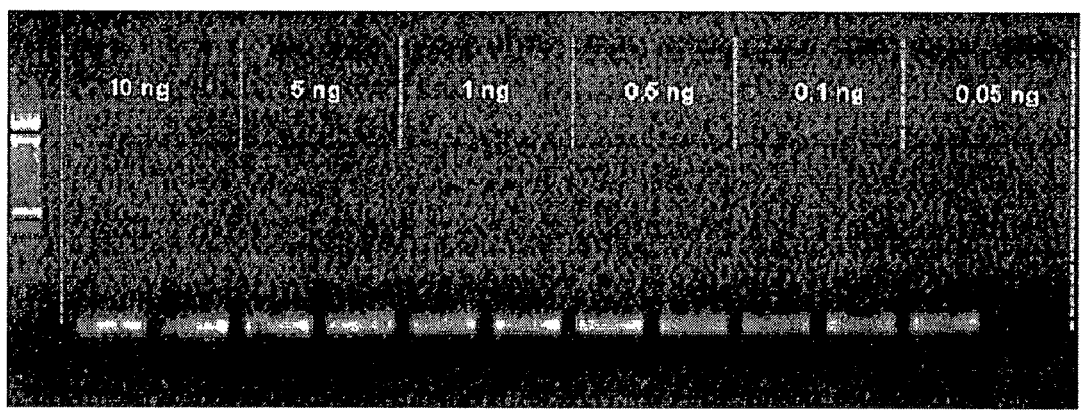
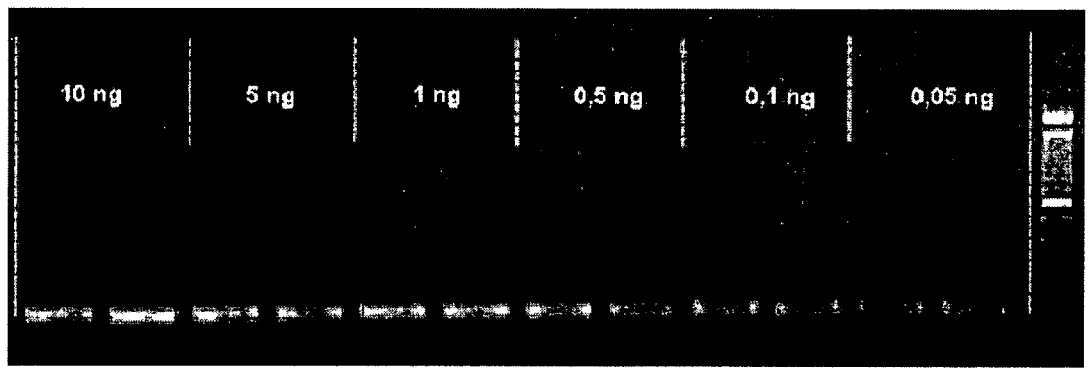

Fig. 11

```
2cf        GTTTTRGTTATTAGTGAGT  (SEQ ID NO:46)
B5+9FT6                 GTGAGTATGTGTGGTTTGTGT-P
                                 (SEQ ID NO:47)
           GTTTTTGTTATTAGTGAGTATGTGTGGTTTGTGTTTTTG
           GGGATGGGGTTTAGAGTTTTTAGTATGGGGTTAATTTGT
           AGTATTAGGTTTGGGTTTTTGGTAGGGTTTTTTGTTTAT
           TTTGAGATTTGGGATGGGGGTTTAGGGGATTTAGGA
                                      (SEQ ID NO:48)
           P-ACTCTAAACCCTACCCCCAAAT (SEQ ID NO:49)B15+17RT11
                       CCAAATCCCCTAAATCCT            2cr
                         (SEQ ID NO:50)
```

Fig. 13
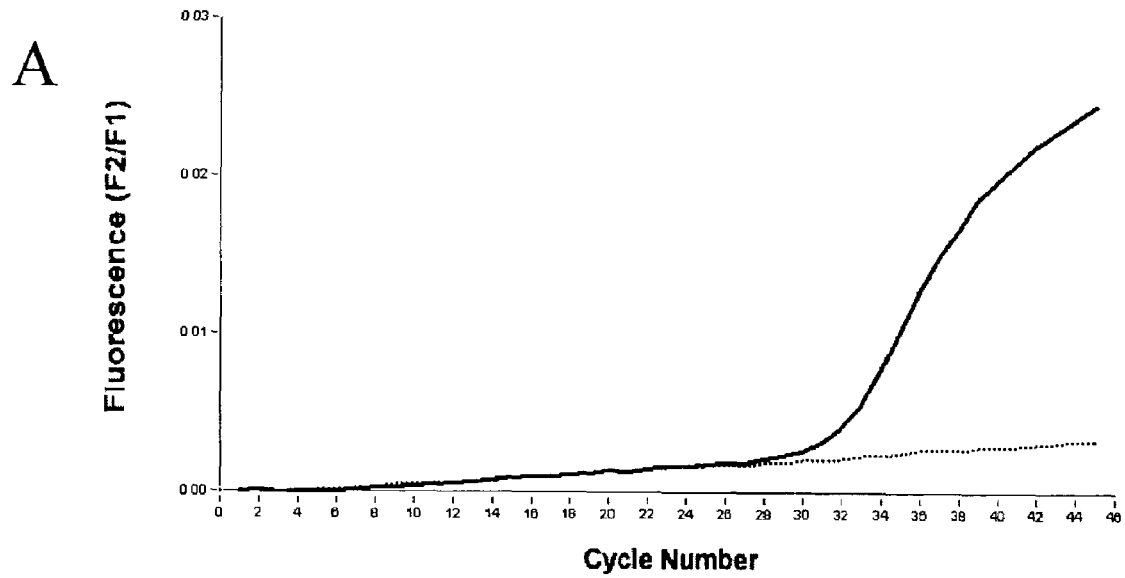
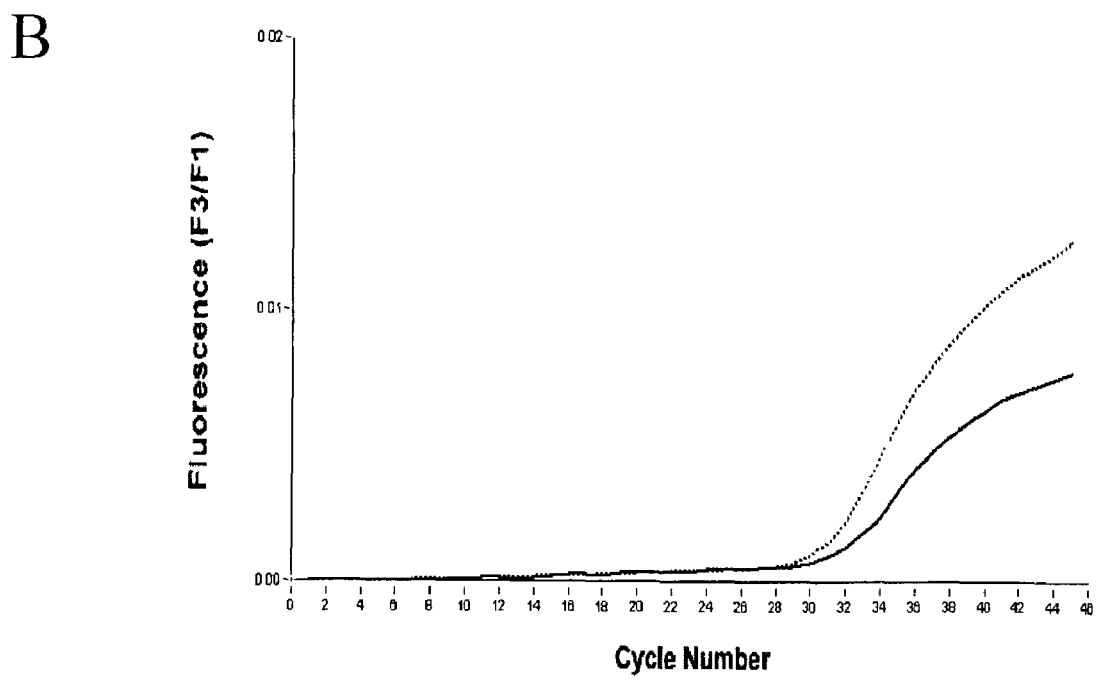

Fig. 14

| Rotor Position | Sample Name | F2/F1 Crossing Point |
|---|---|---|
| 1 | up 100%, 5 ul, F1F2 | 28.95 |
| 2 | up 1:1, 5 ul, F1F2 | 34.80 |
| 3 | up 1:10, 5 ul, F1F2 | 37.46 |
| 4 | up 1:20, 5 ul, F1F2 | 39.39 |
| 5 | up 1:100, 5 ul, F1F2 | 41.32 |
| 6 | up 1:200, 5 ul, F1F2 | |
| 7 | up 1:500, 5 ul, F1F2 | |
| 8 | up 1:1000, 5 ul, F1F2 | |
| 9 | up 100%, 5 ul, F1F2B | 33.38 |
| 10 | up 1:1, 5 ul, F1F2B | 34.41 |
| 11 | up 1:10, 5 ul, F1F2B | 36.84 |
| 12 | up 1:20, 5 ul, F1F2B | 37.67 |
| 13 | up 1:100, 5 ul, F1F2B | 40.81 |
| 14 | up 1:200, 5 ul, F1F2B | |
| 15 | up 1:500, 5 ul, F1F2B | |
| 16 | up 1:1000, 5 ul, F1F2B | |
| 17 | ng F1F2 | |
| 18 | ng F1F1B | |

*Fig. 15*

Sample Information

| Rotor Position | Sample Name | F2/F Crossing Point | F3/F Crossing Point |
|---|---|---|---|
| 1 | up 100% -B | 30.48 | 31.32 |
| 2 | up 1:2 -B | 31.46 | 30.18 |
| 3 | up 1:10 -B | 39.26 | 31.24 |
| 4 | up 1:20 -B | | 30.47 |
| 5 | up 1:100 -B | | 31.60 |
| 7 | up 1:500 -B | | 31.38 |
| 8 | up 1:1000 -B | | 30.68 |
| 9 | down 100% -B | | 31.33 |
| 10 | negativ -B | | |
| 11 | up 100% +B | 31.56 | 31.26 |
| 12 | up 1:2 +B | 32.59 | 31.51 |
| 13 | up 1:10 +B | 35.80 | 34.28 |
| 14 | up 1:20 +B | 37.33 | 36.47 |
| 15 | up 1:100 +B | 42.03 | 42.39 |
| 17 | up 1:500 +B | 42.89 | |
| 18 | up 1:1000 +B | | |
| 19 | down 100% +B | | |
| 20 | negativ +B | | |

HIGHLY SENSITIVE METHOD FOR THE DETECTION OF CYTOSINE METHYLATION PATTERNS

CROSS-REFERENCE TO RELATED APPLICATIONS

The present application is a continuation-in-part of International Application No. PCT/EP02/02572, which has an international filing date of Mar. 8, 2002, and which is incorporated herein by reference. Said international application, which is still pending, has not yet been published, but will be published under PCT Article 21(2) in a language other than English.

BACKGROUND OF THE INVENTION

The present invention concerns a method for the detection of cytosine methylation in DNA samples.

The levels of observation that have been well studied due to method developments in recent years in molecular biology include the genes themselves, as well as transcription and translation of these genes into RNA and the proteins arising there from. During the course of development of an individual, when a gene is turned on and how the activation and inhibition of certain genes in certain cells and tissues are controlled can be correlated with the extent and nature of the methylation of the genes or of the genome. Pathogenic states are also expressed by a modified methylation pattern of individual genes or of the genome.

5-Methylcytosine is the most frequent covalently modified base in the DNA of eukaryotic cells. For example, it plays a role in the regulation of transcription, in genetic imprinting and in tumorigenesis. The identification of 5-methylcytosine as a component of genetic information is thus of considerable interest. 5-Methylcytosine positions, however, cannot be identified by sequencing, since 5-methylcytosine has the same base-pairing behavior as cytosine. In addition, in the case of a PCR amplification, the epigenetic information, which is borne by 5-methylcytosines, is completely lost.

A relatively new method that has since been applied most frequently for investigating DNA for 5-methylcytosine is based on the specific reaction of bisulfite with cytosine, which is converted to uracil, which corresponds in its base-pairing behavior to thymidine, after a subsequent alkaline hydrolysis. In contrast, 5-methylcytosine is not modified under these conditions. Thus the original DNA is converted, such that methylcytosine, which originally cannot be distinguished from cytosine by means of its hybridization behavior, now can be detected by "standard" molecular biological techniques as the single remaining cytosine, for example, by amplification and hybridization or sequencing. All of these techniques are based on base pairing, which now is fully utilized. The prior art, which concerns sensitivity, is defined by a method that incorporates the DNA to be investigated in an agarose matrix, through which diffusion and renaturation of the DNA is prevented (bisulfite reacts only on single-stranded DNA) and all precipitation and purification steps are replaced by rapid dialysis (Olek A., Oswald J., Walter J. A modified and improved method for bisulphate based cytosine methylation analysis. Nucleic Acids Res. 1996 Dec. 15; 24 (24): 5064-6). Individual cells can be investigated with this method, which illustrates the potential of the method. Of course, previously, only individual regions of up to approximately 3000 base pairs in length have been investigated; a global investigation of cells for thousands of possible methylation analyses is not possible. Of course, this method also cannot reliably analyze very small fragments of small sample quantities. These are lost despite the protection from diffusion through the matrix.

A review of the other known possibilities for detecting 5-methylcytosines can be derived from the following review article: Rein T, DePamphilis M L, Zorbas H. Identifying 5-methylcytosine and related modifications in DNA genomes. Nucleic Acids Res. 1998 May 15; 26 (10): 2255-64.

The bisulfite technique has previously been applied only in research, with a few exceptions (e.g., Zeschnigk M, Lich C, Buiting K, Dörfler W, Horsthemke B. A single-tube PCR test for the diagnosis of Angelman and Prade-Willi syndrome based on allelic methylation differences at the SNRPN locus. Eur J Hum Genet. 1997 March-April; 5 (2): 94-8). However, short, specific pieces of a known gene are always amplified after a bisulfite treatment and either completely sequenced (Olek A, Walter J. The pre-implantation ontogeny of the H19 methylation imprint. Nat Genet. 1997 November.; 17(3): 275-6) or individual cytosine positions (Gonzalgo M L, Jones P A. Rapid quantitation of methylation differences at specific sites using methylation-sensitive single nucleotide primer extension (Ms-SNuPE). Nucleic Acids Res. 1997 Jun. 15;25 (12):2529-31; WO 95/00669) or an enzyme cleavage (Xiong Z, Laird P W. COBRA: a sensitive and quantitative DNA methylation assay. Nucleic Acids Res. 1997 Jun. 15;25(12): 2532-4) are detected by a "primer extension reaction". Also, detection by means of hybridizing has been described (Olek et al., WO 99/28498).

Urea improves the efficiency of the bisulfite treatment prior to the sequencing of 5-methylcytosine in genomic DNA (Paulin R, Grigg G W, Davey M W, Piper A A. Urea improves efficiency of bisulphate-mediated sequencing of 5'-methylcytosine in genomic DNA Nucleic Acids Res. 1998 November 1;26(21):5009-10).

Other publications, which are concerned with the application of the bisulfite technique for the detection of methylation in individual genes are: Grigg G, Clark S. Sequencing 5-methylcytosine residues in genomic DNA. Bioassays. 1994 June; 16(6):431-6, 431; Zeschnigk M, Schmitz B, Dittrich B, Buiting K, Horsthemke B, Dörfler W. Imprinted segments in the human genome: different DNA methylation patterns in the Prader-Willi/Angelman syndrome region as determined by the genomic sequencing method. Hum Mol Genet. 1997 March; 6(3):387-95; Feil R, Charlton J, Bird A P, Walter J, Reik W. Methylation analysis on individual chromosomes: improved protocol for bisulphate genomic sequencing. Nucleic Acids Res. 1994 February 25;22(4): 695-6; Martin V, Ribieras S, Song-Wang X, Rio M C, Dante R. Genomic sequencing indicates a correlation between DNA hypomethylation in the 5' region of the pS2 gene and in its expression in human breast cancer cell lines. Gene. May 19, 1995; 157 (1-2): 261-4; WO 97/46705, WO 95/15373 and WO97/45560.

Another known method is so-called methylation-sensitive PCR (Herman J G, Graff J R, Myohanen S, Nelkin B D, Baylin S B. (1996), Methylation-specific PCR: a novel PCR assay for methylation status of CpG islands. Proc Natl Acad Sci USA. Sep. 3; 93 (18): 9821-6). For this method, primers are used, which hybridize either only to a sequence that is formed by the bisulfite treatment of a DNA that is not methylated at the respective position, or, vice versa, primers, which only bind to a nucleic acid which has formed by the bisulfite treatment of a DNA that is methylated at the respected position. With these primers, amplified products can then be produced, whose detection in turn supplies hints of the presence of a methylated or unmethylated position in the sample, to which the primers bind.

A more recent method is also the detection of cytosine methylation by means of a TaqMan PCR, which has become known as "methyl-light" (WO 00/70090). It is possible with this method to detect the methylation status of individual positions or a few positions directly in the course of the PCR, so that a subsequent analysis of the products is spared.

A review of the prior art in oligomer array production can be taken from a special publication of Nature Genetics that appeared in January 1999 (Nature Genetics Supplement, Volume 21, January 1999), the literature cited therein and U.S. Pat. No. 5,994,065 on methods for the production of solid carriers for target molecules such as oligonucleotides with reduced nonspecific background signal.

Probes with many fluorescent labels have been used for the scanning of an immobilized DNA array. Particularly suitable for fluorescent labels is the simple introduction of Cy3 and Cy5 dyes at the 5'-OH of the respective probe. The fluorescence of the hybridized probes is detected, for example, by means of a confocal microscope. The dyes Cy3 and Cy5, in addition to many others, are commercially available.

Matrix-assisted laser desorption/ionization mass spectrometry (MALDI-TOF) is a very powerful development for the analysis of biomolecules (Karras M, Hillenkamp F. Laser desorption ionization of proteins with molecular masses exceeding 10,000 daltons. Anal Chem. 1998 Oct. 15;60 (20): 2299-301). An analyte is embedded in a light-absorbing matrix. The matrix is evaporated by means of a short laser pulse and the analyte molecule is transported unfragmented into the gas phase. The ionization of the analyte is achieved by collisions with matrix molecules. An applied voltage accelerates the ions in a field-free flight tube. The ions are accelerated to a varying extent based on their different masses. Smaller ions reach the detector sooner than larger ions.

MALDI-TOF spectroscopy is excellently suitable for the analysis of peptides and proteins. The analysis of nucleic acids is somewhat more difficult (Gut, I. G. and Beck, S. (1995), DNA and Matrix Assisted Laser Desorption Ionization Mass Spectrometry. Molecular Biology: Current Innovations and Future Trends 1: 147-157.) For nucleic acids, the sensitivity is approximately 100 times poorer than for peptides and decreases overproportionally with increasing fragment size. For nucleic acids, which have a backbone with multiple negative charges, the ionization process through the matrix is essentially less efficient. In MALDI-TOF spectroscopy, the selection of the matrix plays a very important role. For the desorption of peptides, several very powerful matrices have been found, which produce a very fine crystallization. Several high-performing matrices have been found in the meantime for DNA, but the difference in sensitivity has not been reduced in this way. The difference in sensitivity can be reduced by modifying the DNA chemically in such a way that it is similar to a peptide. Phosphorothioate nucleic acids, in which the usual phosphates of the backbone are substituted by thiophosphates, can be converted into a charge-neutral DNA by simple alkylation chemistry (Gut, I. G. and Beck, S. (1995), A procedure for selective DNA alkylation and detection by mass spectrometry. Nucleic Acids Res. 23: 1367-1373). The coupling of a "charge tag" to this modified DNA results in an increase in sensitivity by the same amount that is found for peptides. Another advantage of "charge tagging" is the increased stability of the analysis against impurities, which greatly interfere with the detection of unmodified substrates.

Genomic DNA is obtained by standard methods from DNA of cells, tissue or other test samples.

This standard methodology is found in references such as Fritsch and Maniatis, Molecular Cloning: A Laboratory Manual, 1989.

Accordingly, up until now there have been many methods for methylation analysis in the prior art. The present invention, however, will solve the problem that current methods are unable to solve, i.e., to amplify in a targeted manner a DNA to be investigated that is found in a body fluid or serum, when other, sequence-homologous DNA segments of different origin are also present.

The DNA to be investigated as well as the otherwise present nucleic acids, which are named background DNA below, are usually amplified equally, since the primers used are not able to distinguish between the DNA to be investigated and background DNA. One possibility for distinguishing these DNAs, however, is by the different methylation pattern. A current method is methylation-sensitive PCR, abbreviated MSP (Herman J G, Graff J R, Myohanen S, Nelkin B D, Baylin S B. (1996), Methylation-specific PCR: a novel PCR assay for methylation status of CpG islands. Proc Natl Acad Sci USA. September 3; 93 (18): 9821-6). This method is comprised of several steps. First, a bisulfite treatment is conducted according to the prior art, which in turn leads to the circumstance that all cytosine bases are converted to uracil while the methylated cytosine bases (5-methylcytosine) remain unchanged. In the next step, one now uses primers, which are completely complementary to a methylated DNA converted with bisulfite, but not to a corresponding DNA which was present originally in the unmethylated state. When the PCR is conducted with such a primer, this leads to the fact that the originally methylated DNA is amplified exclusively. It is also possible to use a primer, which, in contrast, amplifies only unmethylated DNA. In this way, if the DNA to be analyzed as well as background DNA are present, the DNA fragments to be investigated will be produced selectively and exclusively, as long as they differ from the background DNA relative to their methylation status in a CpG position. Prior art is now to infer from the detection of such a DNA molecule to be investigated either the methylation state or the presence of a DNA to be investigated, which in turn permits, in principle, a diagnosis, for example, of a tumor disorder in the patient, since it is known, for example, that the serum DNA concentration is in part drastically increased in tumor patients. Only the DNA originating from tumors will be detected in addition to the background DNA. In principle, the analysis of DNA is comparable in other body fluids.

The method that is described here and which is to be considered as the closest prior art, however, has several disadvantages. For example, it is not possible to conclude the quantity present in serum from the detectability of an amplified fragment of the DNA to be investigated. Even minimal quantities of such DNA are successful for obtaining a positive result, which is an advantage, on the one hand, but can also act in a very unfavorable manner, if one wishes to evaluate, for example, the effect of a tumor resection on serum DNA. The greatest disadvantage, however, is that many methylation positions are present, in which the DNA to be investigated and the background DNA differ only in degree. It is obvious that the existing MSP method can only be conducted if one knows that the backbround DNA differs definitively and up to 100% from the DNA to be investigated in the CpG position of interest, if one does not want to risk false positive results. In contrast, it is typical in a tumor tissue that a specific position is present in the methylated state, e.g., in 95% of the tumor cells, in which the otherwise present background DNA, however, is present in the methylated state only to a maximum of 5%, so that it is not possible with the MSP method to produce informative results, since a quantification of the template DNA by means of PCR in principle is not possible or can be accomplished only with increased expenditure. Also, this invention is based on the knowledge that often methylation patterns are present in a DNA fragment, which are typical for a specific type of cell, for example, a tumor cell.

Also, prior art includes a process developed by Epigenomics, which amplifies equally the DNA to be investigated and background DNA after bisulfite treatment and then examines the former CpG positions contained in the fragment by hybridization techniques, and alternatively by means of mini-sequencing or another current method. This has the advantage, that a quantitative pattern is obtained relative to the investigated methylated positions, i.e., the determination of the methylation degree of a multiple number of positions is successfully obtained, which, e.g., makes possible a very accurate classification in the case of solid tumors. The disadvantage of this method, however, is that it cannot supply accurate information in those cases in which the background DNA greatly predominates, since this information is amplified accurately along with the DNA to be investigated and both are analyzed in the mixture. This problem does not exist in the analysis of solid tumors, in which the material to be investigated can be selected in a targeted manner, but the analysis, for example, of serum DNA is made difficult.

DESCRIPTION OF THE INVENTION

The object of the present invention is now to eliminate the disadvantages of the prior art and to combine the advantages of both methods for detection in body fluids and serum.

The object is solved in that a method is created for the detection of cytosine methylation in DNA samples in which the following steps are conducted:

A genomic DNA sample, which comprises the DNA to be investigated and background DNA is chemically treated in such a way that all of the unmethylated cytosine bases are converted to uracil, whereas the 5-methylcytosine bases remain unchanged;

The chemically treated DNA sample is amplified with the use of at least 2 primer oligonucleotides as well as a polymerase, whereby the DNA to be investigated is preferred as the template over the background DNA, and The amplified products are analyzed and conclusions are drawn on the methylation status of the DNA to be investigated, from the presence of an amplified product and/or from the analysis of other positions.

It is preferred according to the invention that the sample DNA is obtained from serum or other body fluids of an individual.

It is further preferred according to the invention that sample DNA is obtained from cell lines, blood, sputum, stool, urine, serum, cerebro-spinal fluid, tissue embedded in paraffin, for example, tissue from eyes, intestine, kidneys, brain, heart, prostate, lungs, breast or liver, histological slides, and all possible combinations thereof.

It is most particularly preferred according to the invention that the chemical treatment is conducted with a bisulfite (=disulfite, hydrogen sulfite). It is also preferred that the chemical treatment is conducted after embedding the DNA in agarose. It is also and additionally preferred that a reagent that denatures the DNA duplex and/or a radical trap is present in the chemical treatment.

It is preferred that the amplification is conducted in the second step in the presence of at least one additional oligonucleotide, which binds to a 5'-CG-3' dinucleotide or a 5'-TG-3' dinucleotide or a 5'-CA-3' dinucleotide, whereby the additional oligonucleotide preferably binds to the background DNA and adversely affects its amplification.

It is particularly preferred that this binding site of the additional oligonucleotide or PNA oligomer overlaps with the binding sites of the primers on the background DNA and the additional oligonucleotide hinders the binding of at least one primer oligonucleotide to the background DNA.

In addition, it is particularly preferred that at least two additional oligonucleotides or PNA oligomers are utilized, whereby their binding sites each overlap in turn with the binding site of one primer on the background DNA, and the additional oligonucleotides and/or PNA oligomers hinder the binding of both primer oligonucleotides to the background DNA.

It is also particularly preferred that one of the additional oligonucleotides and/or PNA oligomers prevents the binding of the forward primer, while the other prevents the binding of the reverse primer.

It is particularly preferred that the additional oligonucleotides and/or PNA oligomers are present in at least five times the concentration of the primer oligonucleotides.

In another particularly preferred variant of the method, the additional oligonucleotides and/or PNA oligomers bind to the background DNA and thus prevent the complete elongation of the primer oligonucleotide in the polymerase reaction. It is particularly the case that the polymerase used does not have 5'-3' exonclease activity. Another preferred variant is that the additional oligonucleotides are present modified at the 5' end and thus cannot be significantly broken down by a polymerase with 5'-3' exonuclease.

In addition, it is preferred according to the invention that the chemically treated DNA sample is amplified in the second step with the use of at least 2 primer oligonucleotides and another oligonucleotide, which hybridizes to a 5'-CG-3' dinucleotide or a 5'-TG-3' dinucleotide or a 5'-CA-3' dinucleotide, and at least one reporter oligonucleotide, which hybridizes to a 5'-CG-3' dinucleotide or a 5'-TG-3' dinucleotide or a 5'-CA-3' dinucleotide, as well as a polymerase; whereby the additional oligonucleotide preferably binds to the background DNA and adversely affects its amplification, and whereby the reporter oligonucleotide binds preferably to the DNA to be investigated and indicates its amplification. It is thus advantageous that another oligomer labeled with a fluorescent dye is used in addition to the reporter oligonucleode so that this other oligomer hybridizes directly adjacent to the reporter oligonucleotide and this hybridization can be detected by means of fluorescence resonance energy transfer. It is further advantageous that a TaqMan assay is conducted. It is also preferable that a LightCycler assay is conducted.

It is further preferred according to the invention that the oligonucleotides used in addition to the primers do not make available a 3'-OH function. In addition, it is preferred that the reporter oligonucleotide bears at least one fluorescent label. It is also preferred that the reporter molecules indicate the amplification either by an increase or a decrease in fluorescence. It is particularly advantageous that the increase or decrease of fluorescence is also directly used for analysis and that the methylation state of the DNA to be analyzed can be concluded from the fluorescent signal.

It is further preferred according to the invention that the background DNA is present in 100 times the concentration of the DNA to be investigated. It is also preferred that the background DNA is present in 1000 times the concentration of the DNA to be investigated.

It is further preferred that the analysis, or, as the case may be, the additional analysis be conducted by means of hybridization to oligomer arrays, whereby oligomers can be nucleic acids or molecules that are similar in their hybridization properties, such as PNAs.

It is also advantageous according to the invention that the oligomers hybridize to the DNA to be analyzed by means of a 12-22 base long segment and they include a CG, TG or CA dinucleotide.

It is preferred that the methylation status of more than 20 methylation positions of the DNA to be analyzed is detected in one experiment.

It is additionally preferred that the methylation status of more that 60 methylation positions of the DNA to be analyzed is detected in one experiment.

It is also preferred according to the invention that the analysis or, as the case may be, the additional analysis is conducted by length measurement of the amplified DNA to be investigated, whereby methods for length measurement comprise gel electrophoresis, capillary gel electrophoresis, chromatography (e.g., HPLC), mass spectrometry and other suitable methods. It is thus also of advantage that methods for sequencing include the Sanger method, the Maxam-Gilbert method and other methods, such as sequencing by hybridization (SBH).

A method is also preferred according to the invention, wherein the sequencing for each CpG position or a small group of these positions is conducted each time with a separate primer oligonucleotide and the primer extension constitutes only one or a few bases and one concludes from the type of primer elongation the methylation status of the respective positions in the DNA to be investigated.

It is also preferred that the presence of a disorder or another medical condition of the patient is concluded from the methylation degree of the different CpG positions investigated.

It is of advantage that the amplified products themselves are provided with a detectable label for detection. It is also advantageous that the labels are fluorescent labels, or/and that the labels are radionuclides or/and that the labels are removable mass labels, which are detected in a mass spectrometer.

It is further preferred that in the amplification, one of the primers is bound to a solid phase.

It is also preferred according to the invention that the amplified products are detected overall in the mass spectrometer and are clearly characterized by their mass.

Another subject of the present invention is also the use of a method according to the invention for the diagnosis and/or prognosis of adverse events for patients or individuals, whereby these adverse events belong to at least one of the following categories: undesired drug interactions; cancer disorders; CNS malfunctions, damage or disease; symptoms of aggression or behavioral disturbances; clinical, psychological and social consequences of brain damage; psychotic disturbances and personality disorders; dementia and/or associated syndromes; cardiovascular disease, malfunction and damage; malfunction, damage or disease of the gastrointestinal tract; malfunction, damage or disease of the respiratory system; lesion, inflammation, infection, immunity and/or convalescence; malfunction, damage or disease of the body as an abnormality in the developmental process; malfunction, damage or disease of the skin, muscles, connective tissue or bones; endocrine and metabolic malfunction, damage or disease; headaches or sexual malfunction.

The use of a method according to the invention is thus advantageous for distinguishing cell types or tissues or for investigating cell differentiation.

The subject of the present invention is also a kit, comprised of a reagent containing a bisulfite, primers and other oligonucleotides without 3'-OH function for the production of amplified products, as well as optionally, instructions for conducting an assay according to the invention.

The present invention thus describes a method for the detection of the methylation state of genomic DNA samples. In contrast to previously known methods, the degree of methylation of a set of CpG positions is determined in a selected subgroup of DNA fragments, e.g. in serum, so that an analysis is also possible in the presence of an excess of diagnostically irrelevant background DNA.

The preferred method is comprised of several steps, which can be summarized as follows:

First, serum and/or other body fluids are obtained from the patient and the DNA found therein is isolated, if necessary. Subsequently, in the second step, a chemical treatment is conducted, preferably with a bisulfite (=hydrogen sulfite, disulfite), wherein, for example, all unmethylated cytosine bases are converted to uracil, but the methylated cytosine bases (5-methylcytosine) remain unchanged. In the third step of the method, an amplification is now conducted, in which preferably the DNA to be investigated is amplified, but not the background DNA, or the latter is amplified only to a smaller extent. In the following fourth step, the amplified fragments are now analyzed for their methylation signature and the degree of methylation of several previous CpG positions is determined in the amplified products. In the fifth step of the method, the presence of a disorder or another medical state of the patient is concluded from the degree of methylation at the different CpG positions investigated.

The essence of the present invention is now that two types of CpG positions play a role and contribute equally to the analysis and these will be named below as "qualifier" positions and "classifier" positions. The qualifier positions serve for the purpose of distinguishing the DNA to be analyzed from the background DNA in the amplification. This can be done in different ways technically, as presented in detail below. The property of these positions, however, is that their degree of methylation in the DNA to be investigated is as different as possible from that in the background DNA and this leads to a preference for the DNA to be investigated in the amplification. The classifier positions, in contrast, serve for the purpose of extracting information that is important for the diagnosis from the amplified product, produced predominantly from the DNA to be investigated, by means of the respective degree of methylation. Up to several hundred such classifier positions can be used for one analysis, if the analysis takes place, for example, on oligomer arrays, although this is often not necessary. However, in this case, it is not the formation of a specific amplified product that is of importance for the investigation result, but rather the analysis of the CpG positions in the same amplified product. In several cases, however, it is surely possible and meaningful to relate the information to be derived from the formation of an amplified product in the analysis; in this case, several positions are then both classifier and qualifier.

The first step of the method, the obtaining of samples, is preferably conducted by obtaining of body fluids, such as, e.g., sputum or serum, but it is obvious that the method can be conducted with many kinds of samples from different sources, which are listed here without claim as to their completeness.

Preferably, the genomic DNA utilized in the method is obtained from a DNA sample, whereby sources for DNA include, e.g., cell lines, blood, sputum, stool, urine, serum, cerebro-spinal fluid, tissue embedded in paraffin, for example, tissue from eyes, intestine, kidneys, brain, heart, prostate, lungs, breast or liver, histological slides and all possible combinations thereof.

In several cases, a purification or concentration of the DNA is conducted prior to the bisulfite treatment, in order to avoid a disruption of the bisulfite reaction and/or the subsequent PCR due to too high a degree of impurities. However, it is known that, for example, a PCR can proceed from tissue after treatment, for example, with proteinase K without further purification, and this is true in a meaningful way also for the bisulfite treatment and subsequent PCR.

The chemical treatment is preferably conducted by treatment with a bisulfite (=hydrogen sulfite, disulfite), again preferably sodium bisulfite (ammonium bisulfite is less suitable). Either the reaction is produced according to a published variant, here preferably the DNA is embedded in agarose in order to keep the DNA in the single-stranded state during treatment, or, however, according to a new variant, by treatment in the presence of a radical trap and a denaturing reagent, preferably an oligoethylene glycol dialkyl ether or, for example, dioxane. Prior to the PCR reaction, the reagents are removed either by washing in the case of the agarose method or by a DNA purification method (prior art, precipitation or binding to a solid phase, membrane) or, however, simply by diluting in a concentration region that does not significantly influence the PCR.

For the third step, it is now essential that the qualifier positions be selected and a suitable method is selected, which permits the selective amplification of the DNA to be investigated. The selection of the positions is made according to the premises that these should distinguish as much as possible between the background DNA and the DNA to be investigated with respect to their methylation. For this purpose, the methylation profiles of the gene segments that are considered each time both for tumors to be investigated as well as also for the background DNA from healthy individuals are determined. Those positions, which have the greatest difference between tumor DNA and background DNA (for example, in serum), are selected as qualifier positions. Such positions are already known for a multiple number of genes, for example for GSTpi, for HIC-1 and MGMT (von Wronski M A, Harris L C, Tano K, Mitra S, Bigner D D, Brent T P. (1992) Cytosine methylation and suppression of O6-methylguanine-DNA methyltransferase expression in human rhabdomyosarcoma cell lines and xenografts. Oncol Res.; 4 (4-5): 167-74; Esteller M, Toyota M, Sanchez-Cespedes M, Capella G, Peinado M A, Watkins D N, Issa J P, Sidransky D, Baylin S B, Herman J G. (2000), Inactivation of the DNA repair gene O6-methylguanine-DNA methyltransferase by promoter hypermethylation is associated with G to A mutations in K-ras in colorectal tumorigenesis. Cancer Res. May 1; 60 (9): 2368-71). There are now several methods, which are preferred overall, by means of which the DNA to be investigated can be preferably amplified with the use of these qualifier positions.

First or all, it is possible to conduct a reaction corresponding to MSP by using primers that hybridize completely to the sequence that corresponds to the DNA to be investigated after bisulfite treatment, but not to the analogously treated background DNA. In other words, the primers hybridize to a DNA segment, in which one or more qualifier positions are found, and only if their methylation status in the original DNA corresponds to that which is characteristic for the DNA to be investigated, can an amplification occur to a significant extent. This is a simple variant in principle, but which has the disadvantage that the qualifier positions must lie each time at one or both ends of the DNA fragment, i.e., the classifier positions must lie between the qualifier positions (or, however, in the case of only one qualifier position, the latter should not lie in the midst of the classifier positions). Although it is preferred according to the invention to conduct such an MSP variant, in fact, it can be used only in comparatively few cases, since the distribution of qualifier and classifier positions will be ideal only in a few cases. However, since in principle, it is simple to conduct, it is listed here as preferred in any case.

A variant is particularly preferred, however, in which the primers do not overlap with a qualifier position or hybridize with the latter, but the PCR amplification is influenced rather by at least one other oligonucleotide, which cannot function as a primer and which binds at a qualifier position.

This means that the chemically treated DNA, in principle, as it is prior art, is amplified by means of two primers. One or more qualifier positions are found within the DNA segment bounded by the two primers. Now in contrast to standard PCR, additional oligonucleotides are added, which bind to these qualifier positions and, in fact, do so selectively, depending on whether the latter were present either methylated or unmethylated prior to the bisulfite treatment. The DNA to be investigated is accordingly preferably amplified if the oligonucleotides to be added bind less effectively to their qualifier positions than to the background DNA. In other words, the oligonucleotides added selectively block the amplification of the background DNA.

Preferably, these added oligonucleotides contain either at least one CG, one TG or one CA dinucleotide. They must additionally have the property that they cannot be elongated by the polymerase utilized in the PCR reaction. This is done preferably by the use of 3'-deoxyoligonucleotides or, however, of oligonucleotides with other functions at the 3' position, for example, 3'-O-acetyl oligonucleotides. Additionally, the decomposition of these oligonucleotides by the polymerase must be prevented. This is done preferably either with the use of a polymerase without nuclease activity or preferably with the use of modified oligonucleotides, which have, for example, thioate bridges at the 5' terminal and thus are resistant to a decomposition.

Another particularly preferred variant is the use of PNA (Peptide Nucleic Acid) oligomers, which are utilized in a meaningful manner as the oligonucleotides in this experiment. The PNA oligomers are not decomposed by the polymerase and they cannot be elongated by the polymerase, so that they are ideally suitable for this variant of the method. Methods for the design and synthesis of DNA oligomers are prior art.

As discussed above, several qualifier positions and also several oligonucleotides, each of which is specific for a methylation status present in the background DNA are used in such methods.

After the selective amplification of the DNA to be investigated, it may now be preferred that the methylation status of several classifier positions are determined according to methods known in and of themselves.

However, it is obvious that even in this case, the formation of a certain PCR fragment itself in the individual case may be of sufficient information value, insofar as, which is also true for MSP, the situation is present that the qualifier position is present unmethylated practically up to 100%, for example, in the background DNA, but it is present in methylated form in the DNA to be investigated. If one now uses in the PCR an oligonucleotide, which binds preferably to the sequence which forms from unmethylated background DNA in the bisulfite treatment, then only one product is formed in the PCR, as long as at least a small quantity of the DNA to be investigated is present in general. This may even be sufficient in the individual case for a diagnosis and it would involve a method that has properties similar to those of MSP. Although such a procedure is not directly preferred, such a method has thus far been unknown and is consequently also considered as belonging to the subject of this invention.

This method that uses methylation specific blocking probes along with methylation insensitive primers we term HeavyMethyl. Without additional CpGs investigated within the fragment, this means additional Classifier positions, this method has properties similar to MSP. It is however considered especially useful and preferable in multiplex reactions as primers can be designed to achieve an optimum sensitivity and reliability of the PCR reaction and methylation specificity of the primers is not an issue. Therefore, primer design is not compromised by having to achieve methylation sensitivity within the same oligonucleotide, because a blocking probe can be added that introduces methylation sensitivity afterwards.

It is also particularly useful to combine HeavyMethyl and MSP in one assay by using methylation specific primers and additionally methylation specific probe. This can be used to achieve an effective suppression of the amplification of the background DNA while the primers preferentially amplify the DNA to be analyzed. This way, potentially very high amounts of background DNA can be present and still only the DNA to be analyzed is amplified, because a group of CpG sites that serve as Qualifier positions will be covered by a methylation specific primer and additionally by the blocking probe(s). This is particularly effective as the primers can be only methylation sensitive in the first step, once a primer is incorporated, even wrongly, in the first cycle the sequence is incorporated into a new template for the next cycles and once a primer bound in a first cycle template material will be available for all the subsequent rounds. By using blocking probes, however, like in HeavyMethyl, in all cycles the background DNA will be continuously suppressed. Therefore, combination of the two technologies will make sense in cases with very high amounts of background DNA present.

This combination of MSP with blocking probes can also be useful in cases with only a small group of CpGs servings Qualifiers. Typically, in an MSP assay both primers are methylation sensitive, therefore two groups of CpGs serve as Qualifier positions that may be far apart. This means that MSP will only work efficiently in cases in which co-methylation of these to groups of CpGs can be expected and both can serve as Qualifier positions. Otherwise, the DNA to be analyzed might not be amplified with sufficient preference.

If only one small group of CpGs is available and still a high amount of background DNA has to be blocked, it is therefore preferred that one part of this group of CpGs is covered by a methylation specific primer and the other part is covered by a methylation specific blocking probe, and the binding site of this non-extendible probe could ideally even overlap with the binding site of the primer. This way, high relative sensitivity, this means highly preferred amplification of the DNA to be analyzed while suppressing the background DNA, can be achieved with only a small group of CpGs as Qualifier positions.

It is therefore a particularly preferred embodiment of the invention that the amplification is conducted in the second step in the presence of at least one additional oligonucleotide, which binds to a 5'-CG-3' dinucleotide or a 5'-TG-3' dinucleotide or a 5'-CA-3' dinucleotide, whereby the other oligonucleotide preferably binds to the background DNA and adversely affects its amplification, and one or more primers in the amplification step additionally cover 5'-CG-3' or 5'-TG-3' dinucleotides or 5'-CA-3' dinucleotides and preferentially bind to a fragment containing either 5'-CG-3' dinucleotides or to a fragment containing 5'-CA-3' or 5'-TG-3' dinucleotides.

In another preferred embodiment of the invention only one primer in this amplification step is methylation specific, this means that it binds after bisulphite treatment either to the 5'-TG-3' or 5'-CA-3' containing template (previously unmethylated) or to the corresponding 5'-CG-3' containing template (previously methylated). The additional, non-extendible oligonucleotide will additionally bind to a sequence close or even overlapping with this primer and will also bind methylation-specifically, this means to fragments either previously (before bisulphite treatment) methylated or unmethylated in the sequence context CG.

It is preferred that several fragments are produced simultaneously in a PCR reaction, i.e., that a multiplex PCR is conducted. Care must be taken in its design that not only the primers, but also the additional oligonucleotides used must not be complementary to one another; otherwise a high degree of multiplexing would be more difficult in this case than is usually the case. However, one has the advantage in the case of bisulfite-treated DNA, that a forward primer can never function also as a reverse primer, based on the different G and C content of the two DNA strands, which in turn facilitates the multiplexing and substantially compensates for this disadvantage.

In the simplest case, the fragments that form are now detected. All possible known molecular biological methods are considered for this detection, such as gel electrophoresis, sequencing, liquid chromatography or hybridizations, without analyzing the classifier oligonucleotides. This would also be conceivable for a qualitative control of the preceding method steps. As stated above, however, the subsequent analysis of the degree of methylation of the classifier positions is particularly preferred.

There are a number of possibilities for advantageously combining the preferred amplification of the DNA to be investigated by means of the above-described method with detection techniques for the classifier oligonucleotides.

Detection techniques which are particularly suitable are hybridization to oligomer arrays and, for example, primer extension (mini-sequencing) reactions. The hybridization to oligomer arrays may be used without an additional change of protocol relative to the closest prior art (Olek A, Olek S, Walter J; WO 99/28498). However, it is preferred to hybridize the amplified products to an array of oligomers, which is comprised of pairs of oligonucleotides immobilized to a solid phase, one of which hybridizes each time most preferably to a DNA segment containing an originally unmethylated CpG (classifier position) and the other of which, again most preferably, hybridizes to the corresponding segment in which a methylated CpG was originally contained, each time prior to the bisulfite treatment and amplification. In this case, it is particularly preferred that the amplified product or amplified products be fluorescently or radioactively labeled or labeled with a removable mass tag, so that after the hybridization, the fragments bound to the two oligonucleotides of a pair can be detected and quantified on the basis of this label. An intensity ratio is obtained, from which can be determined, for example, the degree of methylation at the respective classifier position, after calibration of the experiment with completely methylated and unmethylated DNA. A multiple number of fragments and classifier positions can be detected simultaneously on such an oligomer array (FIG. 1). It is meaningful and preferred that the array also contains oligomers detecting qualifier positions for monitoring the experiment, since the ratio of the DNA to be investigated entering into the analysis, to the background DNA, can be determined.

Primer extension reactions may also be conducted on oligonucleotides immobilized on a solid phase. Although it is not absolutely necessary, the immobilization of these primers is preferred, since usually, a multiple number of classifier positions comprised of several amplified products will be investigated and this investigation can be conducted on a solid phase, thus on an oligomer array, in a significantly simpler manner and in one experiment. It is particularly preferred that the primers are found directly next to a classifier position and that the elongation proceeds by only one nucleotide. It is particularly preferred that only dideoxythymidine and dideoxycytidine be added as nucleotides and that each of these is labeled with a different fluorescent dye, whereby, of course, other different labels are also conceivable and even preferred, such as mass tags. After a bisulfite treatment and amplification, previous methylated CG is present as CG while previous unmethylated CG is now present as TG. The primer extension reaction thus either leads to the incorporation of a dideoxycytidine or dideoxythymidine. The degree of methylation of the respective position can be concluded from the ratio of the fluorescent labels detected each time for these two terminators. It is also possible and preferred in this case to conduct the primer extension with dideoxycytidine and dideoxythymidine, if no guanine derivative is present and consequently the primer extension terminates without anything further at a TG or CG sequence even after one base. It is also preferred to conduct the analysis analogously on the counterstrand by distinguishing CA and CG appropriately with dideoxy-ATP and didioxy-GTP or their derivatives.

A particularly preferred variant of the method, however, is the simultaneous detection of qualifier positions and classifier positions in one experiment, which can be achieved by the use of TaqMan or LightCycler technology variants. Additional fluorescently labeled oligonucleotides are to be added to the oligonucleotides, which provide for a preferred amplification of the DNA to be investigated, and the change in fluorescence is measured during the PCR reaction. In principle, since the DNA to be investigated is amplified, information on the methylation status of different classifier CpG positions is obtained predominantly also directly from this change in fluorescence. Since different oligonucleotides are each preferably provided with different fluorescent dyes, a distinction of the change in fluorescence during the PCR is also possible, separately for different positions.

This change in fluorescence that is dependent on the methylation status can be achieved by numerous methods, two of which will be described here by way of example.

First of all, oligonucleotide probes can be used, which bind specifically either to a sequence, which has arisen due to chemical treatment of a DNA unmethylated at the corresponding position or, however, corresponding to a sequence, which has formed by chemical treatment of a DNA methylated at the corresponding position. These probes are most preferably provided with two fluorescent dyes, a quencher dye and a fluorescent dye serving as a marker. Both of these are coupled with the same oligonucleotide probe. Now, if a PCR reaction occurs with the DNA to be investigated as the template, then the PCR reaction will be blocked this time by the fluorescently labeled oligomer probe. However, since the latter is not resistant to the nuclease activity of the polymerase, a decomposition of the probe bound to the template DNA occurs during the PCR reaction, which correlates with the binding efficiency of the probe to the template, since the unbound probe is not decomposed by the polymerase. Due to the fact that the quencher dye and the fluorescent dye serving as the marker are separate from one another The decomposition of the probe is now directly visible because there is an increase of the fluorescence of the marker dye. In principle, this involves a variant of the so-called TaqMan assay.

Accordingly, what is measured is the formation of the PCR product from the DNA to be investigated, but only if the investigated classifier position is also present in the methylation state, which the probe can detect by hybridizing to the chemically treated DNA. A counter-sample containing a probe, which would correspondingly bind to the classifier position in the other methylation state is thus appropriate and preferred.

Different fluorescent dyes with different emission wavelengths are preferably used on several probes together with a quencher, in order to achieve the ability to distinguish between the probes and thus provide a multiplexing.

Even in the case of such an assay, oligonucleotides binding to the qualifier positions are used, which prevent a significant amplification of the background DNA. The amplification of the DNA to be investigated may also be analyzed in such a way that the same position is also investigated with a probe as described above and the amplification is accordingly detected by a probe binding to a qualifier position. In this case, it is particularly preferred that the oligonucleotide that cannot be decomposed selectively binds to the background DNA, while the fluorescently labeled probe binds to the DNA to be investigated. In a particularly preferred variant of the method, the probe and the non-decomposable oligonucleotide have the same sequence except for preferably one nucleobase, but in any case no more than two nucleobases.

A variant is also particularly preferred, in which several methylatable positions are defined as qualifier positions and at least one oligonucleotide preferably binding to the background DNA as well as a probe are used for these positions. Since the amplification of the background DNA in this case will be suppressed by several oligonucleotides, this method is particularly suitable in cases in which the excess of background DNA is particularly high in comparison to the DNA to be investigated. In many cases, in the case of these variants and the presence of several qualifier positions in one fragment, the further investigation of classifier positions will be made superfluous, since with currently available devices, an arbitrarily large number of different dyes cannot be detected simultaneously (for the most part, these different dyes number 4-5). The investigation of additional classifier positions is then preferably conducted with one of the other detection techniques mentioned above.

It is also preferred that the degree of methylation of several positions can be investigated simultaneously with one probe.

If a more accurate quantification of the degree or methylation of classifier positions is desired, then preferably two probes that compete with one another can preferably be used with different dyes, whereby again, one of these binds in the case of an unmethylated position in the DNA to be investigated, while the other one preferably binds in the opposite case, in the case of a methylated position. The degree of methylation of the investigated position can be concluded from the ratio of the fluorescent increases for the two dyes.

A basically different method, in which, however, a fluorescence change also occurs during the PCR, is currently known as the LightCycler™ technology. The fact is utilized that a fluorescence resonance energy transfer (FRET) can only occur between two dyes, if they are found in the direct vicinity of one another, i.e. 1-5 nucleotides apart. Only then can the second dye be excited by the emission of the first dye and then in turn, emit light of another wavelength, which is then detected.

In the present case of methylation analysis, a hybridization of a fluorescently-labeled probe results at the respectively chemically treated DNA at a classifier position, and the binding of this probe in turn depends on whether the DNA to be investigated was present in methylated or unmethylated form at this postion. Another probe with another fluorescent dye binds directly adjacent to this probe. The latter binding takes place preferably again dependent on methylation, if another methylatable position is present in the respective sequence segment. During the amplification, the DNA is now multiplied, for which reason even more fluorescently-labeled probes bind adjacent to the respective position, inasmuch as the latter had the methylation state required for this, and thus an increasing FRET is measured.

A multiplexing with several different fluorescently labeled probes preferably also occurs with this method.

It is also possible and preferred here that a qualifier position is measured. It is assumed that the background DNA is present in unmethylated form at the respective position and after chemical treatment and amplification, a TG dinucleotide results at this position, and that in contrast, the methylated DNA to be investigated produces a CG dinucleotide, a fluorescently labeled probe would bind to the sequence containing a CG, while a competitive oligomer, which is not labeled, binds to the corresponding TG sequence of the background DNA.

It is thus important that the unmethylated oligonucleotide prevents the amplification due to its clearly higher melting point in contrast to shorter probe oligonucleotides. In this regard, since probes and oligomers binding to the chemically treated background DNA are not identical in this case, except for a few bases, they are essentially longer (by 5-15 bases). Also, it is again possible and preferred to utilize modified oligonucleotides and/or PNAs. In this case also, all probes and oligonucleotides are blocked except for the primers at their 3' end, in order to avoid an elongation in the PCR. This can be done, for example, with a phosphate group.

The two methods differ in principle as a result of the fact that in one case a decrease in fluorescence is measured, while in the other case, an increase in fluorescence is measured. In both cases, both qualifier and classifier positions can be measured.

In summary, a method for the detection of cytosine methylation in DNA samples is particularly preferred in which the following steps are conducted: First, a genomic DNA sample, which contains the DNA to be investigated as well as background DNA, is chemically treated in such a way that all unmethylated cytosine bases are converted to uracil, while the 5-methylcytosine bases remain unchanged; then the chemically treated DNA sample is amplified with the use of at least two primer oligonucleotides as well as a polymerase, whereby the DNA to be investigated is preferred over the background DNA as the template, and in the next step, the amplified products are analyzed and the methylation status in the DNA to be investigated is concluded from the presence of an amplified product and/or from the analysis of additional positions.

In a particularly preferred variant of the method, the sample DNA is obtained from serum or other body fluids of an individual. It is also preferable that the sample DNA is obtained from cell lines, blood, sputum, stool, urine, serum, cerebro-spinal fluid, tissue imbedded in paraffin, for example tissue from eyes, intestine, kidneys, brain, heart, prostate, lungs, breast or liver, histological slides and all possible combinations thereof.

In particularly preferred variant of the method, the chemical treatment is conducted with a bisulfite (=disulfite, hydrogen sulfite). It is preferable to conduct the chemical treatment after embedding the DNA in agarose. It is also preferred that a reagent denaturing the DNA duplex and/or a radical trap is present in the case of the chemical treatment.

In a particularly preferred variant of the method, the amplication is conducted in the second step in the presence of at least one additional oligonucleotide, which binds to a 5'-CG-3' dinucleotide or a 5'-TG-3' dinucleotide or a 5'-CA-3' dinucleotide, whereby the other oligonucleotide preferably binds to the background DNA and adversely affects its amplification.

It is also particularly preferred that at least one of the primers in the amplification step preferentially binds to the DNA to be investigated.

It is further preferred that this binding site of the additional oligonucleotide or PNA oligomer overlaps with the binding sites of the primers on the background DNA and the additional oligonucleotide hinders the binding of at least one primer oligonucleotide to the background DNA.

It is also especially preferred that at least two other oligonucleotides or PNA oligomers are utilized, wherein their binding sites again overlap each time with the binding site of a primer to the background DNA and the additional oligonucleotides and/or PNA oligomers hinder the binding of both primer oligonucleotides to the background DNA. Thereby it is further preferred according to the invention that one of the additional oligonucleotides and/or PNA oligomers hinders the binding of the forward primer, while the other one hinders the binding of the reverse primer.

It is also preferred that the additional oligonucleotides and/or PNA oligomers are present in at least five times the concentration in comparison to the primer oligonucleotides.

It is further preferred that the additional oligonucleotides and/or PNA oligomers bind to the background DNA and thus hinder the complete elongation of primer oligonucleotides in the polymerase reaction. Thereby it is especially preferred that the polymerase used has no 5'-3' exonuclease activity. But it is also preferred that the additional oligonucleotides are present modified at the 5' end and thus cannot be significantly broken down by a polymerase with 5'-3' exonuclease activity.

It is also particularly preferred that the chemically treated DNA sample is amplified in the second step with the use of at least 2 primer oligonucleotides and another oligonucleotide, which hybridizes to a 5'-CG-3' dinucleotide or a 5'-TG-3' dinucleotide or a 5'-CA-3' dinucleotide, and at least one reporter oligonucleotide, which hybridizes to a 5'-CG-3'-dinucleotide or a 5'-TG-3'-dinucleotide or a 5'-CA-3'-dinucleotide, along with a polymerase; whereby the additional oligonucleotide preferably binds to the background DNA and adversely affects its amplification and whereby the reporter oligonucleotide preferably binds to the DNA to be investigated and indicates its amplification.

It is also preferred that in addition to the reporter oligonucleotide, another oligomer which is labeled with a fluorescent dye is used, which hybridizes directly adjacent to the reporter oligonucleotide and this hybridization can be detected by means of fluorescence resonance energy transfer (FRET).

A TaqMan assay is preferably conducted for the analysis. It is also preferred to conduct a LightCycler assay (as described above).

The oligonucleotides used in addition to the primers most preferably do not make available a 3'-OH function. Also, the reporter oligonucleotide most preferably bears at least one fluorescent label.

It is particularly preferred that the reporter molecules indicate the amplification either by an increase or a decrease in the fluorescence and that the increase or decrease in fluorescence is also used directly for the analysis, and the methylation state of the DNA to be analyzed is concluded from the fluorescent signal.

According to the invention it is preferred that the background DNA is present in 100 times the concentration of the DNA to be investigated.

According to the invention it is further preferred that the background DNA is present in 1000 times the concentration of the DNA to be investigated.

In a particularly preferred embodiment of the invention for the amplification step mentioned above, the amplication is conducted in the second step in the presence of at least one additional oligonucleotide, which binds to a 5'-CG-3' dinucleotide or a 5'-TG-3' dinucleotide or a 5'-CA-3' dinucleotide, whereby the other oligonucleotide preferably binds to the background DNA and adversely affects its amplification, and one or more primers in the amplification step additionally cover 5'-CG-3' or 5'-TG-3' dinucleotides or 5'-CA-3' dinucleotides and preferentially bind to a fragment containing either 5'-CG-3' dinucleotides or to a fragment containing 5'-CA-3' or 5'-TG-3' dinucleotides.

In another preferred embodiment of the invention only one primer in this amplification step is methylation specific, this means that it binds after bisulphite treatment either to the 5'-TG-3' or 5'-CA-3' containing template (previously unmethylated) or to the corresponding 5'-CG-3' containing template (previously methylated). The additional, non-extendible oligonucleotide will additionally bind to a sequence close or even overlapping with this primer and will also bind methylation-specifically, this means to fragments either previously (before bisulphite treatment) methylated or unmethylated in the sequence context CG.

In a particularly preferred variant of the method, the analysis or the additional analysis is conducted by means of hybridizing to oligomer arrays, wherein oligomers can be nucleic acids or molecules that are similar in their hybridization properties, such as PNAs. Preferably, the oligomers hybridize by means of a 12-22 base long segment to the DNA to be analyzed and comprise a CG, TG or CA dinucleotide. The methylation status of more than 20 methylation positions of the DNA to be investigated is detected preferably with this method in one experiment, and most preferably, there are more that 60 methylation positions.

A method is also particularly preferred in which the additional analysis is conducted by measuring the length of the amplified DNA to be investigated, whereby methods for this length measurement include gel electrophoresis, capillary gel electrophoresis, chromatography (e.g., HPLC), mass spectrometry and other suitable methods.

A method is also particularly preferred, in which the additional analysis is conducted by sequencing, whereby methods for sequencing include the Sanger method, the Maxam-Gilbert method and other methods such as sequencing by hybridization (SBH). Again a method is preferred, wherein the sequencing (according to Sanger) is conducted for each of the CpG positions or for a small group of these positions, each time with a separate primer oligonucleotide, and the extension of the primer constitutes only one base or just a few bases, and the methylation status of the respective positions in the DNA to be investigated is concluded from the type of primer extension.

In a particularly preferred variant of the method, the presence of a disease or another medical condition of the patient is concluded from the degree of methylation at the different CpG positions that are investigated.

In a particularly preferred manner, the amplified products are also provided with a detectable label for their detection. These labels preferably involve fluorescent labels, radionuclides or removable mass labels, which are detected in a mass spectrometer.

In addition, a method is preferred, in which one of the primers is bound to a solid phase in the amplification.

A variant of the method is also preferred, wherein the amplified products are detected as a whole in the mass spectrometer and thus are clearly characterized by their mass.

Another subject of the present invention is the use of one of the described methods for the diagnosis and/or prognosis of events detrimental to patients or individuals, wherein these adverse events belong to at least one of the following categories: undesired drug interactions; cancer diseases; CNS malfunctions, damage or disease; symptoms of aggression or behavioral disturbances; clinical, psychological and social consequences of brain damage; psychotic disturbances and personality disorders; dementia and/or associated syndromes; cardiovascular disease, malfunction and damage; malfunction, damage or disease of the gastrointestinal tract; malfunction, damage or disease of the respiratory system; lesion, inflammation, infection, immunity and/or convalescence; malfunction, damage or disease of the body as an abnormality in the developmental process; malfunction, damage or disease of the skin, the muscles, the connective tissue or the bones; endocrine and metabolic malfunction, damage or disease; headaches or sexual malfunction.

In addition, the use of one of the described methods is preferred for differentiating cell types or tissues or for investigating cell differentiation.

Another subject of the present invention is a kit, comprised of a reagent containing bisulfite, primers and additional oligonucleotides without 3'-OH function for the production of amplified products, as well as, optionally, instructions for conducting at least one of the described variants of the method.

The following examples explain the invention:

EXAMPLE 1

Methylation-Sensitive Amplification of the MDR1 Gene with the use of PNA Blocking Probes (PCR Clamping) in the MDR-1 Gene.

a) Methylation-specific PCR with PNA Probes (PNA Blocking Probes), whose Binding Sites do not Overlap with those of the Primers.

First, PCR conditions were defined for bisulfite-treated DNA, by which an allele-specific influence of the PNA blocking probe on the PCR can be recognized. In this first experiment, the binding sites between PNA and the primers do not overlap.

First, the influence of an 11-mer PNA of the sequence AAAATGTGTT was tested in a PCR with the primers TAAGTATGTTGAAGAAAGATTATTGTAG and TAAAAACTATCCCATAATAACTCCCAAC. An effect of the PNA on the PCR reaction cannot be measured under standard PCR conditions with an annealing temperature of 55° C. The standard cycler program used for the amplification of the MDR-1 fragment uses the following program steps:

| | |
|---|---|
| Step 1: T = 96° C. | 20 min |
| Step 2: T = 96° C. | 30 s |
| Step 3: T = 56° C. | 1.15 min |
| Step 4: T = 72° C. | 2.00 min |
| Steps 2 to 4 are conducted for 40 cycles. | |
| Step 5: T = 72° C. | 15 min |
| Step 6: Cool to 4° C. and maintain temperature. | |

Consequently, the primer lengths, the annealing temperature and the PNA sample length must be optimally adapted in order to achieve an allele-specific suppression of the amplification.

In order to make possible an optimal annealing for primers and PNAs, shorter 21-mer primers TAAGTATGT-TGAAGAAAGATT and AATCCCCATAAACTTACCAAA were tested with a longer 13-mer PNA AAAGACGTGT-TAT. Additional tests were conducted with 18, 19 and 20-mer primers, which differ from the above sequences only by the fact that bases were omitted at the 3' end. The 21-mer primers were tested with a gradient of annealing temperature. In a parallel batch, the 13-mer PNA AAAGACGTGT-TAT or the PNA AAAGATGTGTTAT adapted for a sequence produced from an unmethylated allele were added in different concentrations of 20-100 pmol/μl.

A clear influence on the PCR was observed with annealing temperatures of 49.4° C. and 46.7° C. with addition of PNA in a concentration of 70 and 100 pmol/μl. The effect was clearest with the use of an 18-mer primer.

It was now investigated as to how much a lower elongation temperature of 54° C. affects the inhibiting influence of PNAs.

Each of the above-named 13-mer PNAs or both 13-mer PNAs were added together, in a concentration of 50 and 70 pmol/μl to the PCR batch for this purpose. A clear suppression of the PCR could be observed in comparison to the positive control without PNAs (FIG. 2, agarose-gel electrophoresis, concentrations of the PNAs for the 13-mer PNA probes used; annotation: MDR 1-5 FM: 13-mer PNA AAA-GACGTGTTAT; MDR 1-5 FU: 13-mer PNA AAAGATGT-GTTAT; pos. Kontrolle=positive control; neg. Kontrolle=negative control; 100 bp Leiter=100-bp ladder). The tests make it obvious that the DNAs used in the tests were present predominantly unmethylated at the positions of interest, which could be confirmed by bisulfite sequencing. Therefore, a clear allele specificity of the PNA blocking probe can be shown in this experiment, which leads to a preferred amplification of the unmethylated fragments.

b) Methylation-specific PCR with PNA Probes (PNA Blocking Probes), whose Binding Sites Overlap with those of the Primers ("Primer Exclusion").

In the above experiments, the primers were selected in such a way that the PNA target sequence lay approximately in the center of the region to be amplified. The arrangement was described as more sensitive if the primer and PNA sequence were adjacent to each other or overlapped. In the case of a sequence-specific binding of the PNA, with this arrangement, an effect of the PNA could be observed even with smaller PNA concentrations.

A primer with the sequence TTATGTGAATTTTGAAAG is selected for this experiment such that it overlaps with the PNA sequence (primer exclusion). Both 13-mer PNAs AAAGACGTGTTAT and AAAGATGTGTTAT were added to reaction batches in 3 different concentrations.

A complete suppression of the PCR reaction was obtained even with a concentration of 25 pmol/μl. In the previous experiment, a complete suppression of the PCR could be recognized with the addition of both PNAs only when the concentration reached 70 pmol/μl.

c) Primer Exclusion with Fragments Corresponding to Unmethylated DNA

For the detection of a sequence-specific binding, the effect of PNAs on templates well-characterized relative to methylation status was investigated in additional experiments. The template DNA used for this experiment corresponded to a bisulfite-treated completely unmethylated DNA.

This was used as the template in a PCR. The following program steps were utilized for this:

| | |
|---|---|
| Step 1: T = 96° C. | 20 min |
| Step 2: T = 96° C. | 30 s |
| Step 3: T = 49° C. | 1.15 min |
| Step 4: T = 54° C. | 2.00 min |
| Steps 2 to 4 were run for 36 cycles. | |
| Step 5: T = 72° C. | 15 min |
| Step 6: cool to 4° C. and maintain temperature. | |

The 13-mer PNAs as described above were added in 3 different concentrations to the reaction batches. In this case of the unmethylated template, one would expect that the PNA MDR 1-5-FU (3) adapted to this template would have a clearly stronger influence than MDR 1-5-FM (3). It is shown in FIG. 3 (for annotation, see FIG. 2) that this is in fact the case even for comparatively low PNA concentrations.

These results show that the suppression of the PCR reaction makes possible methylation-specific amplifications due to specifically binding PNAs. In control experiments with PNAs not complementary to MDR-1, it could be shown that these exercise no noteworthy influence on the PCR at the concentrations in question (not shown).

EXAMPLE 2

Methylation-Sensitive Amplification of a Fragment of the GSTpi Gene.

Specific CpG positions of the GSTPi gene were identified as tumor markers for prostate cancer. In a pair of primers selected for the experiments, GGAAAGAGGGAAAG-GTTTT and TACTAAAAACTCTAAACCCCAT, a primer is localized such that it precisely bounds the PNA sequence CCCCGAAAACGCG (or CCCTGAAAATGTG). The PNA sequence contains three relevant CpG positions now in distinction to those PNAs used for the MDR1 fragment. The relevant CpGs of the GSTPi fragments are present in "normal" DNA unmethylated, i.e., DNA not originating from tumor patients. The PNA "GSTP-down" of the sequence CCCTGAAAATGTG which is given for the reaction batch should thus have a recognizable influence on the PCR reaction, but not the corresponding PNA "GSTP-up" CCCCGAAAACGCG.

The PNA "GSTP-down" was added in three different concentrations to the test batch. A gradient of the annealing temperature was tested.

The results of the experiment are shown in FIG. 4 (for annotation see FIG. 2). The strongest suppression of PCR can be determined by addition of the PNA (GSTP-down) at an annealing temperature of 55° C. In comparison to the positive control (without addition of PNA) it can be recognized that the PCR reaction could be significantly suppressed by the addition of the PNA in a concentration of 20 pmol/μl.

Subsequently, the influence of the PNAs "GSTP-up" and GSTP-down" on the amplification of an unmethylated DNA in the original sample and a methylated DNA originating from a prostate tumor tissue as the template was compared in order to detect a sequence-specific (and thus in final analysis, a methylation-sensitive) binding.

The unmethylated DNA and the prostate DNA were utilized as the templates in PCR. The PNAs "GSTP-up" or "GSTP-down" were added in three different concentrations to the reaction batches.

The addition of the "GSTP-down" PNA has a visible influence on the down-methylated template: the PCR is completely suppressed when PNA is added in a concentration of 70 pmol/μl. In the case of the addition of the PNA "GSTP-up" PNA, on the other hand, only a weak inhibiting influence of the PNA on the PCR can be recognized.

The addition of the "GSTP-up" PNA to the test DNA of prostate tissue, however, has a considerable inhibiting influence on the PCR (FIG. 5 (Prostata=prostate)). The addition of the PNA in a concentration of 20 pmo/μl clearly suppresses the PCR. A complete suppression of the PCR can be determined with an addition of PNA in a concentration of 50 pmol/μl. In contrast to this, the addition of the "GSTP-down" PNA to the prostate DNA has a clearly smaller influence. Even an addition of the PNA in a concentration of 70 pmol/μl does not completely suppress the PCR.

The experiments show that it is possible, by means of blocking oligomer probes, to suppress selectively the amplification of methylated or unmethylated alleles at defined positions. In the sense of this invention, the respective positions would serve as qualifier positions, i.e., one would selectively suppress the amplification of undesired methylated templates of the background DNA.

EXAMPLE 3

Different Possibilities for the Use of Probes Suppressing the PCR in a Methylation-Specific Manner on the Example of the GSTPi Gene.

FIG. 6 shows several possibilities of how to arrange the primers in the sense of a methylation-sensitive application for a given template sequence. For explanation, FIG. 6a shows the templates present after the bisulfite treatment: DNA 1 corresponding to an originally methylated DNA sample and DNA 2 corresponding to an originally unmethylated DNA sample.

FIG. 6b shows the arrangement of one of the primers in the sense of an allele-specific PCR or a methylation-specific PCR (MSP). In this case, only the amplification of the methylated DNA 1 could occur with the use of the primer shown.

FIG. 6c and 6d show how correspondingly unmethylation-specific primers can be used, either by the use of degenerated positions (6c) or universal bases (here, inosine) in FIG. 6d.

Several possibilities are presented in FIG. 7, of how the primers and probes ("blockers") are to be arranged in the sense of a methylation-sensitive amplification in the case of a given template sequence. In these examples, the primers used are not themselves methylation-specific, but the methylation specificity is achieved only by the. probes ("blockers"). Specific probes are utilized each time as blockers for DNA 1 and DNA 2.

Primers and probes do not overlap in FIG. 7a, but the probes are directly connected to the 3' end of the primer. The probe shown is an oligonucleotide modified at the 3' end, which cannot be elongated itself in the amplification. Analogously, PNAs may also be used, but which must be shorter in this example, however, corresponding to their melting temperature. The same primer is used in FIG. 7b, but here the DNA probe overlaps with the primer (primer exclusion).

In FIGS. 7c and 7d, a primer provided with degenerated positions and the methylation-specific probe overlap. Universal bases may also be used analogously in the primers.

An example is shown analogously with forward and reverse primers in FIG. 8, in which a probe is used, which does not overlap with any of the primers.

These examples will illustrate the numerous possibilities of how oligomer probes can be utilized for methylation-specific amplification in order to suppress background DNA in comparison to the DNA to be analyzed. The scope of the invention, however, will not be limited to the embodiments described here as examples.

EXAMPLE 4

Preparation of Unmethylated and Methylated DNA and Bisulfite Treatment.

For the preparation of methylated DNA, human genomic DNA was treated with S-adenosylmethionine and CpG methylase (Sssl, New England Biolabs) according to the instructions of the manufacturer. For the preparation of unmethylated DNA, the gene fragment ELK-1 was amplified with the primers GCTCTATGGTCTTGTCTAACCGTA and AGGTGGTGGTGGCGGTGG proceeding from human genomic DNA, by means of PCR. The thus-prepared unmethylated and methylated DNA, as well as human genomic DNA was treated with bisulfite (hydrogen sulfite, disulfite) in such a way that all of the cytosines not methylated at the 5-position of the base are modified so that a base that differs in its base-pairing behavior is formed, whereas the cytosines methylated in the 5-position remain unchanged. If bisulfite is used for the reaction in the concentration range between 0.1 mole and 6 moles, an addition occurs at the unmethylated cytosines bases. Also, a denaturing reagent or solvent as well as a radical trap must be present. A subsequent akaline hydrolysis then leads to the conversion of unmethylated cytosine nucleobases to uracil. This converted DNA serves for the purpose of detecting methylated cytosines.

23

EXAMPLE 5

Preparation of Cy5-Labeled Gene Probes

Starting with the DNA samples treated with bisulfite, a defined fragment of length of 595 bp from the promoter region of the ELK-1 gene is amplified. The amplification is conducted with the primer oligonucleotides ATGGTTTTGTTTAATYGTAGAGTTGTTT and TAAACCCRAAAAAAAAAAACCCAATAT. By using primer oligonucleotides, which are labeled with the fluorescent dye Cy5, the fragment is labeled directly in the PCR. Bisulfite (hydrogen sulfite, disulfite)-treated (1) unmethylated DNA, (2) methylated DNA or (3) human genomic DNA is used as the matrix DNA. Then these three different DNA fragments are investigated in separate hybridizations for their degree of methylation at a specific CpG position.

EXAMPLE 6

Conducting the Hybridization and Evaluating a Hybridized DNA "Chip"

The gene probes prepared in Example 5 are hybridized on a DNA chip. Oligonucleotides have been immobilized beforehand on the chip. The oligonucleotide sequences are derived from the amplified fragment of the gene ELK-1 named in Example 2, and represent CG dinucleotides, including their direct vicinity. The length of the oligonucleotides amounts to 14-22 nucleotides, and the position of the CG dinucleotide within the oligonucleotide is variable. After hybridization, the DNA chip is scanned (see FIG. 1), and the hybridization signals are numerically evaluated (data not shown). The results of the hybridization for the oligonucleotides CTACTCAACGAAAACAAA and CTACTCAACAAAAACAAA are shown in FIG. 1. Here CTACTCAACGAAAACAAA preferably hybridizes if the cytosine of the ELK-1 fragment which is found at position 103 of the amplified product is methylated, and CTACTCAACAAAAACAAA hybridizes, if this cytosine is unmethylated.

A DNA chip is shown in FIG. 1 after hybridization with the promoter fragment. The pseudocolor image is shown as it is produced after scanning. In contrast to the black-white figure shown here, a color picture is produced by the scanner. The intensity of the different colors represents the degree of hybridization, whereby the degree of hybridization decreases from red (these can be recognized as light spots in FIG. 1) to blue (these can be recognized as dark spots in FIG. 1).

EXAMPLE 7

Production of Template DNA and Establishing the GSTp1 PCR

Human DNA from peripheral blood (Promega, Madison [Wis.] USA), which has been untreated and methylated enzymatically in vitro, which was subjected to a bisulfite treatment, was used as the template DNA. For the methylation of all CG dinucleotides, 6 µg of DNA in a reaction volume of 150 µl were reacted with SssI (New England Biolabs, Frankfurt/Main) according to the directions of the manufacturer. The bisulfite treatment was conducted according to a published method (Olek A, Oswald J, Walter J. A modified and improved method for bisulphate based cytosine methylation analysis. Nucleic Acids Res. 1996 December 15; 24 (24: 5064-6).

24

A 153-bp GSTp1 fragment (positions 1242-1393) in the Sequence Acc. No. M24485.1) was amplified with the bisulfite-DNA specific primers 2cf GTTTT (CT) GTTATTAGTGAGT and 2cr TCCTAAATCCCCTAAACC in a reaction volume of 25 µl (1×reaction buffer, Qiagen; 1 U of HotstarTaq, Qiagen; 200 µM of each dNTP, 500 nM of each primer, 0.05-10 ng of bisulfite-treated template DNA) under the following PCR conditions (95° C.—15 min; 46 cycles: 96° C.—0:45 min, 52° C.—0:45 min, 72° C.—0:20 min; 72° C.—10 min) (see FIGS. 9 and 10). It could be shown by sequencing of the GSTp1 fragments that human DNA from peripheral blood has no methylated CG dinucleotides for this fragment, while on the other hand, all CG dinucleotides are present in the methylated form in the SssI-treated DNA (see FIG. 9). The sequencing of the GSTp1 fragment confirms other results (see e.g., WO 99/55905), that in the GSTp1 gene, in contrast to the published sequence (Genbank Acc No. M24485.1), an additional G nucleotide is present (between positions 1273 and 1274 in Genbank Acc. No. M24485.1; position 33 in the GSTp1 PCR fragment, see FIG. 9). With respect to the PCR efficiency, there is no difference between CpG-methylated and CpG-unmethylated template DNA (see FIG. 10).

EXAMPLE 8

Selective Amplification of Methylated GSTp1 Fragments.

The experimental design for the selective amplification of methylated GSTp1 fragments is shown schematically in FIG. 11. The amplification of the GSTp1 fragment with the primers 2cf GTTTT(CT)GTTATTAGTGAGT and 2cr TCCTAAATCCCCTAAACC on unmethylated template DNA is prevented by two blocker oligonucleotides (B5+9FT6, GTGAGTATGTGTGGTTTGTGT-P; B15+17RT11, TAAACCCCCATCCCAAATCTCA-P, see FIG. 11) whose sequences correspond to the unmethylated, bisulfite-treated DNA. These oligonucleotides are modified at the 3' end by a phosphate group in order to prevent their elongation during the PCR. The PCR was conducted in a reaction volume of 25 µl with the following cycler program (95° C.—15 min; 46 cycles: 96° C.—0:45 min, 52° C.—0:45 min, 72° C.—0:20 min; 72° C.—10 min). The PCR batch was comprised as follows: 1×reaction buffer (Qiagen, Hilden) 2 U of HotstarTaq (Qiagen, Hilden); 200 µM of each dNTP, 500 nM of each primer, 10 µm of each blocker (B5+9FT6, GTGAGTATGTGTGGTTTGTGT-P and B15+17RT11, TAAACCCCCATCCCAAATCTCA-P), 20 ng –20 pg of bisulfite-treated template DNA. Under these PCR conditions, it was possible to completely suppress the amplification of the GSTp1 fragment relating to 25 µg of unmethylated template DNA (see FIG. 12A, lane 8). If the PCR was conducted without blocker oligonucleotides, the GSTp1 fragment was amplified (see FIG. 12D, lane 8). In contrast, the GSTp1 PCR product could be detected under the same PCR conditions, with and without blocker oligonucleotides, on 100 pg of methylated template DNA (see FIG. 12C, lane 7; 12F lane 7). The absolute sensitivity of the PCR thus lies at least at 100 pg of methylated template DNA.

In order to investigate the relative sensitivity of the PCR, mixtures of unmethylated and methylated template DNA were prepared, in which the ratio of unmethylated to methylated DNA amounted to 1:1 to 1000. For the preparation of these DNA mixtures, human DNA from peripheral blood (Promega, Madison [Wis.] USA) was mixed with SssI-treated DNA (see Example 7), corresponding to the ratios to be obtained and then subjected to a bisulfite treatment. The results of the PCR on these template DNA mixtures (25 µg of total DNA) conducted with and without blocker oligonucleotides, are shown in FIG. 12A, B or FIG. 12D, E. They show that one copy of the methylated GSTp1 gene can be reproducibly detected in a background of 200 copies of unmethylated GSTp1 gene (see FIG. 12A, lane 6; B, lane 6). A relative sensitivity of 1:1000 appears attainable by further optimization of the PCR conditions (see FIG. 12B, lane 7).

The sequence analyses of the PCR products, amplified from the DNA mixture (1:200, ratio of unmethylated to methylated DNA), with blocker (see FIG. 12A, lane 6) and without blocker (see FIG. 12D, lane 6) showed the expected results. The PCR product produced in the PCR without blocker corresponded to an unmethylated GSTp1 gene, while in contrast, the GSTp1 gene fragment which was produced in the PCR with blocker oligonucleotides had a methylated epigenetic status.

Other 3' modifications, such as ddNTP or additional nucleotides, which cannot correspond to the corresponding GSTp1 nucleotide sequence, were also successfully tested.

EXAMPLE 9

Selective Amplification of Methylated GSTp1 Fragments on a LightCycler.

The LightCycler (Roche) is a device for conducting PCR and simultaneous detection and analysis of the PCR products. The device was manipulated according to the manufacturer's instructions. The quantitative and qualitative analyses of the PCR were conducted with LightCycler Software Version 3.5.

The selective amplification of methylated GSTp1 gene fragments was conducted in 10 µl of reaction volume (1×reaction buffer (Qiagen, Hilden) 5 U of HotstarTaq (Qiagen, Hilden); 200 µM of each dNTP, 625 nM of each primer (2cf GTTTT(CT) GTTATTAGTGAGT; 2cr TCCTAAATCCCCTAAACC, 4 µM blocker (B5+9 FT16, GTGAGTATGTGTGGTTTGTGTT-P), 0.25 µg/µl BSA (Sigma, Munich), 250 nM anchor oligonucleotide (GSTp1-Fluo, TTTAGAGTTTTTAGTATGGGGTTAATT-fluorescein; TibMolBiol, Berlin), 250 nM hybridizing probe (GSTp1-red 705, red 705-GTATTAG-GTTTGGGTTTTTGGT-P; TibMolBiol, Berlin) and/or GSTp1-red 650, red 650-TAGTATTAGGT-TCGGGTTTTCGG-P, TibMolBiol, Berlin), 20 ng -200 pg of template DNA) with the following cycler program: 95° C.—15 min; 46 cycles: denaturation 96° C.—4 s, annealing 52° C.—30 s; extension 72° C.—20 s.

Detection was conducted at each amplification cycle by gene-specific and methylation-specific LightCycler detection probes in the annealing step after 10 s. The GSTp1-PCR fragment was detected when both the methylation-nonspecific anchor probe, GSTp1 Fluo as well as one of the methylation-specific probes GSTp1-red 705 or GSTp1-red 650 hybridize with the PCR fragment.

In order to check the methylation specificity of the detection probes, 15 ng of each bisulfite-treated methylated and unmethylated template DNA were amplified in the LightCycler. For detection, the PCR contained the anchor probe GSTp1-Fluo and an equimolar mixture of the hybridizing probes GSTp1-red 705 and GSTp1-red 650. The fluorescence of the probe was measured in the F2/F1 detection channel of the LightCycler for the methylated GSTp1 gene, GSTp1-650, while in contrast, the probe for the unmethylated GSTp1 gene, GSTp1-red 705 is detected in the F3/F1 channel (see FIG. 13). The experiments showed that GSTp1-red 650 specifically detects the methylated GSTp1 gene, and the unmethylated version did not produce a fluorescent signal (see FIG. 13A). The probe GSTp1-red 705, in contrast, detects the unmethylated and the methylated GSTp1 gene, but detects the latter with significantly reduced efficiency (see FIG. 13B).

The absolute and relative sensitivities of the amplification of the methylated GSTp1 fragment were investigated analogously to Example 8. For the determination of the absolute sensitivity, the GSTp1-PCR was conducted on different quantities of methylated, bisulfite-treated template DNA in the LightCycler with and without blocker oligonucleotide. In addition to the "anchor" probe, the hybridizing probe, GSTp1-red 650, was used for the detection. The results are compiled in FIG. 14. The calculation of "crossing points" was produced by the LightCycler Software Version 3.5 and indicates the number of PCR cycles, in which the GSTP1 PCR product could be detected for the first time with a higher signal than the negative control. This means the lower the "crossing point" value is, the more efficient the amplification of the GSTp1 fragment was. If the "crossing point" is not indicated, this means that no PCR product could be detected. In the experiment shown, the GSTp1 could be amplified with 75 pg of methylated, bisulfite-treated template DNA, even in the presence of the blocker (see FIG. 14).

For the determination of the relative sensitivity, PCR of GSTp1 was conducted with 20 ng of template DNA mixtures (see Example 8) with and without blocker oligonucleotides (FIG. 15). For the detection, the PCR contains the "anchor" probe GSTp1-Fluo and an equimolar mixture of hybridizing probes GSTp1-red 705 and GSTp1-red 650. The fluorescence of the probe for the methylated GSTp1 gene, GSTp1-red 650 was measured in the F2/F1 detection channel of the LightCycler, while in contrast, the probe for the unmethylated GSTp1 gene, GSTp1-red 705, is detected in the F3/F1 channel.

The determined "crossing points" showed that in a PCR with blocker oligonucleotide, one copy of the methylated GSTp1 gene can be detected reproducibly in a background of 500 copies of unmethylated GSTP1 gene (see FIG. 15, "rotor position" 17, F2/F1 column). This corresponds to an absolute sensitivity of 40 pg of methylated template DNA. Without blocker oligonucleotides, only a relative sensitivity of 1:10 could be achieved (see FIG. 15, "rotor position" 3, F2/F1 column). Under the same conditions, the amplification of the GSTp1 gene from 15 ng of unmethylated, bisulfite-treated template DNA is completely suppressed (see FIG. 15, "rotor position" 19 and 9, F3/F1 column).

EXAMPLE 10

Selective Amplification of Methylated GSTp1 Fragments on a TaqMan

The TaqMan (Applied Biosystems, Weiterstadt) is another device for conducting PCR and simultaneous detection and analysis of the PCR products. The device was manipulated according to the manufacturer's instructions. The quantitative and qualitative analyses of the PCR were made with the TaqMan Software.

The selective amplification of methylated GSTp1 gene fragments was conducted in 20 µl of reaction volume (1×reaction buffer (Applied Biosystems); 2 U of AmplitaqGold (Applied Biosystems); 3.5 mM $MgCl_2$, 400 µM of each dNTP, 500 nM of each primer (2cft, GTTTT(CT) GTTATTAGTGAGTA; 2cr, TCCTAAATCCCCTAAACC, blocker 1, 7.5 μM (B5+9 FT6, GTGAGTATGTGTG-GTTTGTGT-P), blocker 2, 7.5 μM (B15+17RT19, TAAAC-CCCCCATCCCAAATCTC-P), 450 nM TaqMan probe (Taq1, Blackhole-TAATTCGTAGTATTAGGT-TCGGGTTTTCGGTAGGG-FAM; Biosearch Technologies, 10 ng of template DNA) with the following cycler program: (95° C.—10 min; 3 cycles: denaturation 96° C.—15 s, annealing 60° C.—60 s; 3 cycles: denaturation 96° C.,—15 s, annealing 58° C.—30 s; extension 60° C.—30 s; 3 cycles: denaturation 96° C.—15 s, annealing, 55° C.—30 s, extension 60° C.—30 s; 40 cycles: denaturation 96° C.—15 s, annealing, 52° C.—30 s, extension 60° C.—40 s). Detection was made for each amplification cycle by the gene-specific TaqMan probes after the elongation step.

In order to determine the relative sensitivity, PCR of GSTp1 was conducted with 10 ng of template DNA mixtures (see Example 8) with and without blocker oligonucleotides (FIG. 16). The calculation of the "threshold cycle" was made by the TaqMan software and gives the number of PCR cycles at which the GSTP1 PCR product can be detected for the first time with a higher signal than the negative control, comparable to the "crossing point" values of the LightCycler. This means that the lower the "threshold cycle" value is, the more efficient the amplification of the GSTp1 fragment was.

The determined "threshold cycle" values showed that in a PCR with blocker oligonucleotide, one copy of the methylated GSTp1 gene can be detected in a background of 200 copies of the unmethylated GSTp1 gene (see FIG. 16). This corresponds to an absolute sensitivity of 50 pg of methylated template DNA. Under the same conditions, the amplification of GSTP1 gene from 10 ng of unmethylated bisulfite-treated template DNA was completely suppressed (see FIG. 16).

DESCRIPTION OF THE FIGURES

FIG. 10: Agarose gel of GSTp1 PCR fragments. The PCR was conducted with 10 ng, 5 ng, 1 ng, 0.5 ng and 0.1 ng of methylated (A) and unmethylated (B) bisulfite-treated template DNA.

FIG. 11: Sequence of the GSTp1 fragment with positions of the primers and blocker oligonucleotides.

FIG. 13: Analysis of the methylation specificity of the detection probes. The figure shows the course for fluorescence during the GSTp1 PCR of methylated bisulfite-treated DNA (solid line) and unmethylated, bisulfite-treated DNA (dotted line), detected with hybridization probe GSTp1-red 650 (A) or GSTp1-red 705 (B).

FIG. 14: Determination of the absolute sensitivity of the GSTp1 PCR on the LightCycler. The GSTp1 PCR was conducted with blocker nucleotide ("rotor positions" 9, 10, 11, 12, 13, 14, 15, 16, 18) and without blocker oligonucleotide ("rotor positions" 1, 2, 3, 4, 5, 6, 7, 8, 17). The following was used as template DNA: methylated, bisulfite-treated DNA: 7.5 ng ("rotor positions" 1, 9), 3.7 ng ("rotor positions" 2, 10), 0.75 ng ("rotor positions 3, 11), 0.37 ng ("rotor positions" 4, 12), 0.075 ng ("rotor positions" 5, 13), 0.037 ng ("rotor positions" 6, 14), 0.015 ng ("rotor positions" 7, 15), 0.0075 ng ("rotor positions" 8, 16), and no DNA ("rotor positions" 17, 18).

FIG. 15: Determination of the relative sensitivity of the amplification of the methylated GSTp1 gene. The amplification of the methylated GSTp1 gene was conducted with the LightCycler. The detection is indicated with hybridizing probes GSTp1-red 650 (F2/F1, Crossing Point) and GSTp1-red 705 (F3/F1, Crossing Point). The GSTp1 PCR was conducted with blocker oligonucleotide ("rotor positions" 11, 12, 13, 14, 15, 17, 18, 19, 20) and without blocker oligonucleotide ("rotor positions" 1, 2, 3, 4, 5, 7, 8, 9, 10). The following was used as the template DNA: 15 ng of methylated, bisulfite-treated DNA ("rotor positions" 1, 11) and 15 ng of unmethylated, bisulfite-treated DNA ("rotor positions" 10, 20), methylated and unmethylated, bisulfite-treated DNA in the mixing ratio 1:2 ("rotor positions" 2, 12), 1:10 ("rotor positions" 3, 13), 1:20 ("rotor positions" 4, 14), 1:100 ("rotor positions" 5, 15), 1:500 ("rotor positions" 7, 17), 1:1000 ("rotor positions" 18), and no DNA ("rotor positions" 10, 20).

SEQUENCE LISTING

<160> NUMBER OF SEQ ID NOS: 40

Figure 1:
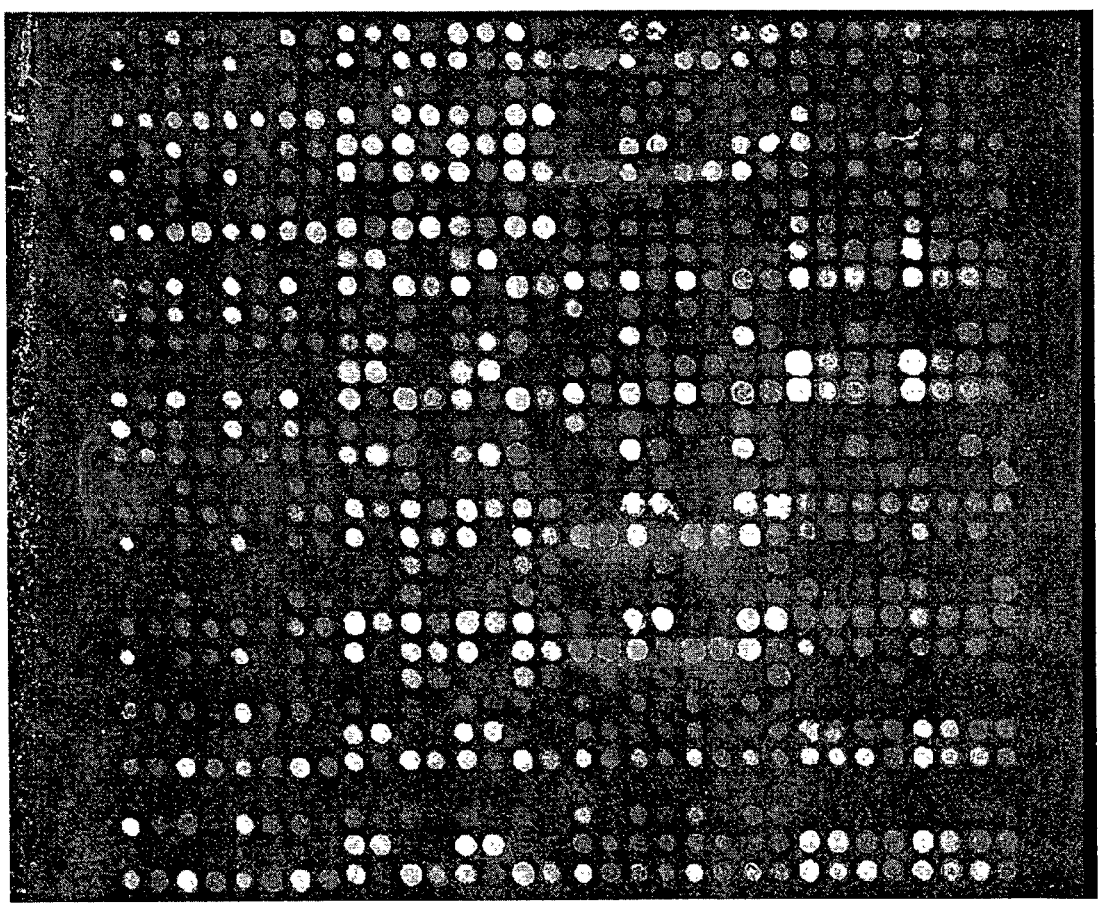
Figure 2:
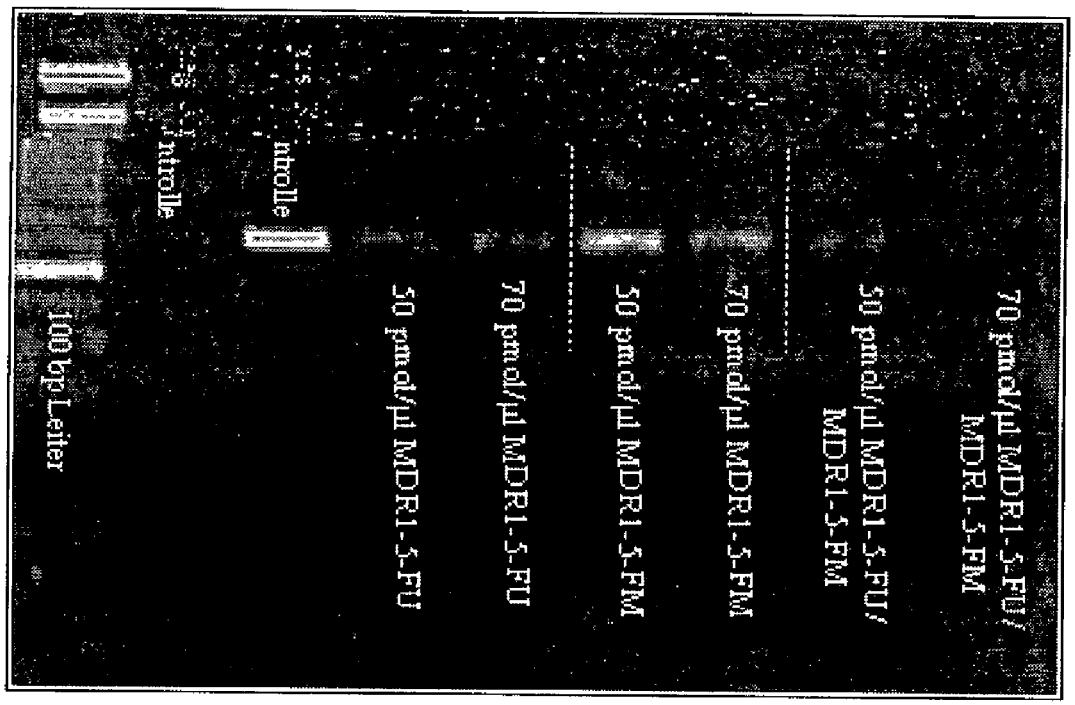
Figure 3:
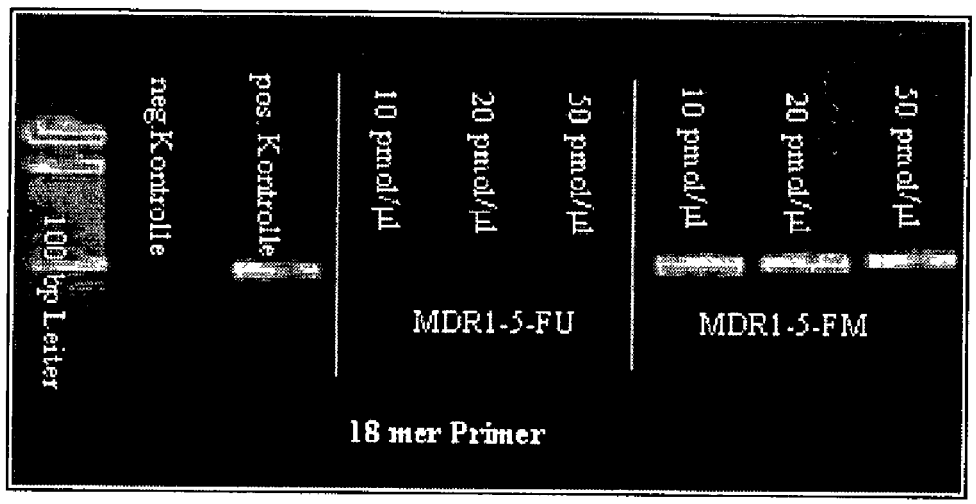
Figure 4:
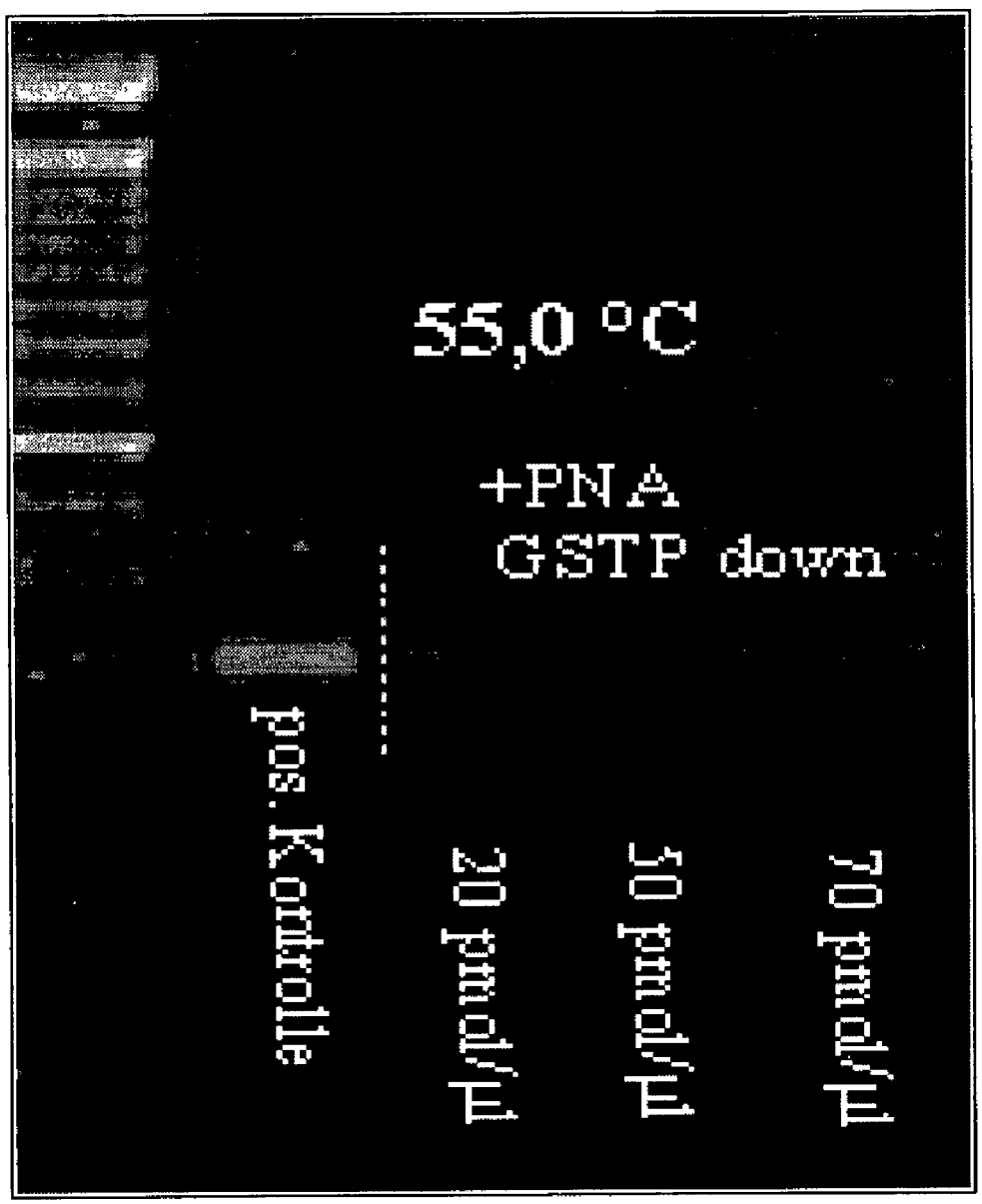
Figure 5:
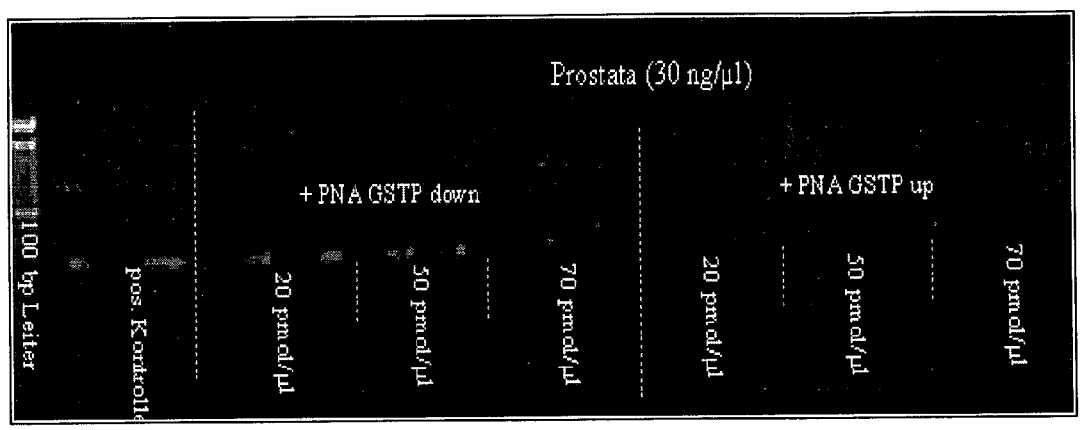
Figure 12:
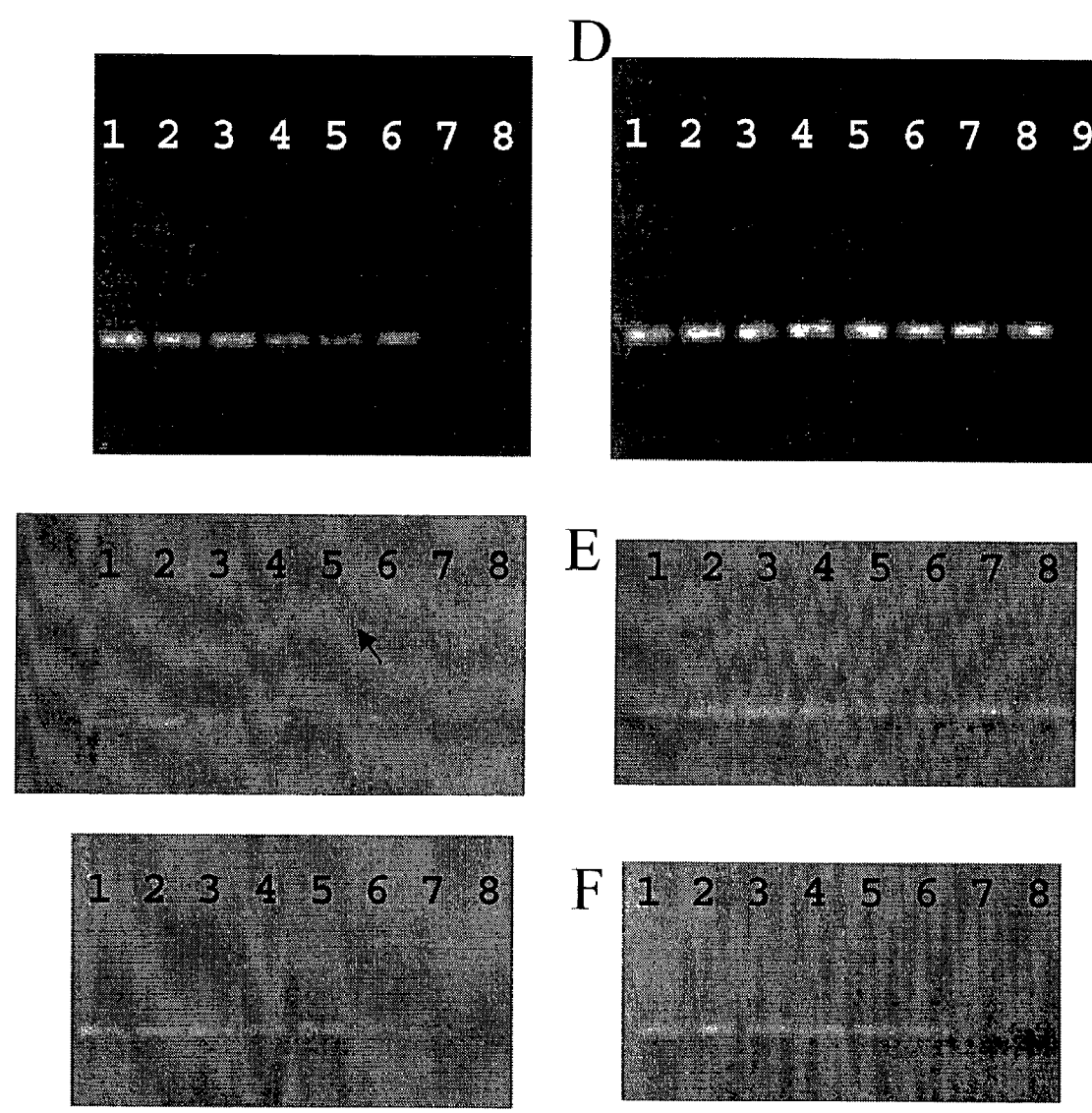
FIG. 12: Agarose gels of GSTp1 PCR fragments. The relative sensitivity of the amplification of the methylated GSTp1 gene (A, B, D, E) and absolute sensitivity (C, F) of the amplification of the methylated GSTp1 gene were analyzed. The GSTp1 PCRs were conducted with blocker oligonucleotide (A, B, C) and without blocker oligonucleotide (D, E, F). The following were used as the template DNA: 20 ng of methylated bisulfite-treated DNA (A1, B1, D1, E1, C1, F1, C2, F2) and 20 ng of unmethylated bisulfite-treated DNA (A8, B8, D8, E8); methylated and unmethylated, bisulfite-treated DNA in the mixing ratio of 1:2 (A2, B2, D2, E2), 1:10 (A3, B3, D3, E3), 1:20 (A4, B4, D4, E4), 1:100 (A5, B5, D5, E5), 1:200 (A6, B6, D6, E6), 1:1000 (A7, B7, D7, E7); 10 ng (C3, F3), 2 ng (C4, F4), 1 ng (C5, F5), 0.2 ng (C6, F6), 0.1 ng (C7, F7), 0.02 ng (C8, F8), methylated, bisulfite -treated DNA and no DNA (A9, D9).
Figure 16:
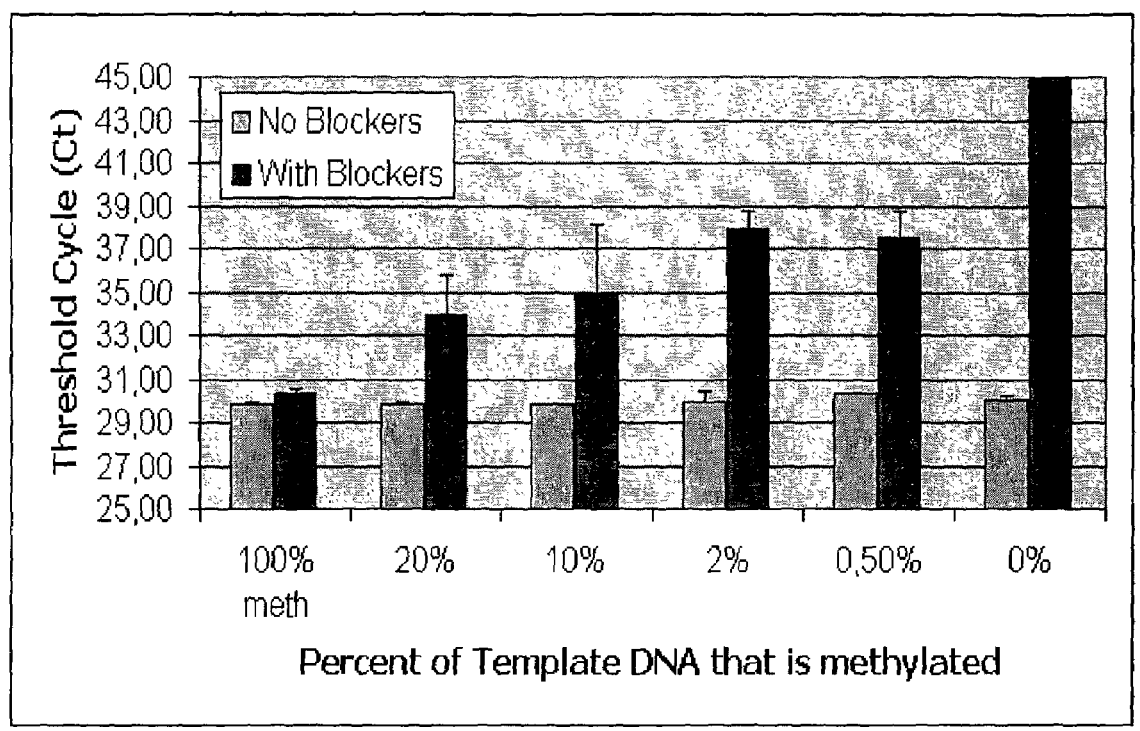
FIG. 16: Determination of the relative sensitivity of the amplification of the methylated GSTp1 gene. The amplification of the methylated GSTp1 gene was conducted with TaqMan.

<210> SEQ ID NO 1
<211> LENGTH: 28
<212> TYPE: DNA
<213> ORGANISM: Artificial Sequence
<220> FEATURE:
<223> OTHER INFORMATION: primer

<400> SEQUENCE: 1
taagtatgtt gaagaaagat tattgtag                                28

```
<210> SEQ ID NO 2
<211> LENGTH: 28
<212> TYPE: DNA
<213> ORGANISM: Artificial Sequence
<220> FEATURE:
<223> OTHER INFORMATION: primer

<400> SEQUENCE: 2
taaaaactat cccataataa ctcccaac                                     28

<210> SEQ ID NO 3
<211> LENGTH: 21
<212> TYPE: DNA
<213> ORGANISM: Artificial Sequence
<220> FEATURE:
<223> OTHER INFORMATION: primer

<400> SEQUENCE: 3
taagtatgtt gaagaaagat t                                            21

<210> SEQ ID NO 4
<211> LENGTH: 21
<212> TYPE: DNA
<213> ORGANISM: Artificial Sequence
<220> FEATURE:
<223> OTHER INFORMATION: primer

<400> SEQUENCE: 4
aatccccata aacttaccaa a                                            21

<210> SEQ ID NO 5
<211> LENGTH: 18
<212> TYPE: DNA
<213> ORGANISM: Artificial Sequence
<220> FEATURE:
<223> OTHER INFORMATION: primer

<400> SEQUENCE: 5
ttatgtgaat tttgaaag                                                18

<210> SEQ ID NO 6
<211> LENGTH: 19
<212> TYPE: DNA
<213> ORGANISM: Artificial Sequence
<220> FEATURE:
<223> OTHER INFORMATION: primer

<400> SEQUENCE: 6
ggaaagaggg aaaggtttt                                               19

<210> SEQ ID NO 7
<211> LENGTH: 22
<212> TYPE: DNA
<213> ORGANISM: Artificial Sequence
<220> FEATURE:
<223> OTHER INFORMATION: primer

<400> SEQUENCE: 7
tactaaaaac tctaaacccc at                                           22

<210> SEQ ID NO 8
<211> LENGTH: 24
<212> TYPE: DNA
<213> ORGANISM: Artificial Sequence
<220> FEATURE:
<223> OTHER INFORMATION: primer
```

```
<400> SEQUENCE: 8
gctctatggt cttgtctaac cgta                                    24

<210> SEQ ID NO 9
<211> LENGTH: 18
<212> TYPE: DNA
<213> ORGANISM: Artificial Sequence
<220> FEATURE:
<223> OTHER INFORMATION: primer

<400> SEQUENCE: 9
aggtggtggt ggcggtgg                                           18

<210> SEQ ID NO 10
<211> LENGTH: 28
<212> TYPE: DNA
<213> ORGANISM: Artificial Sequence
<220> FEATURE:
<223> OTHER INFORMATION: primer

<400> SEQUENCE: 10
atggttttgt ttaatygtag agttgttt                                28

<210> SEQ ID NO 11
<211> LENGTH: 27
<212> TYPE: DNA
<213> ORGANISM: Artificial Sequence
<220> FEATURE:
<223> OTHER INFORMATION: primer

<400> SEQUENCE: 11
taaacccraa aaaaaaaaac ccaatat                                 27

<210> SEQ ID NO 12
<211> LENGTH: 18
<212> TYPE: DNA
<213> ORGANISM: Artificial Sequence
<220> FEATURE:
<223> OTHER INFORMATION: oligonucleotide

<400> SEQUENCE: 12
ctactcaacg aaaacaaa                                           18

<210> SEQ ID NO 13
<211> LENGTH: 18
<212> TYPE: DNA
<213> ORGANISM: Artificial Sequence
<220> FEATURE:
<223> OTHER INFORMATION: oligonucleotide

<400> SEQUENCE: 13
ctactcaaca aaaacaaa                                           18

<210> SEQ ID NO 14
<211> LENGTH: 20
<212> TYPE: DNA
<213> ORGANISM: Artificial Sequence
<220> FEATURE:
<223> OTHER INFORMATION: primer

<400> SEQUENCE: 14
gttttctgtt attagtgagt                                         20

<210> SEQ ID NO 15
```

```
<211> LENGTH: 18
<212> TYPE: DNA
<213> ORGANISM: Artificial Sequence
<220> FEATURE:
<223> OTHER INFORMATION: primer

<400> SEQUENCE: 15
tcctaaatcc cctaaacc                                               18

<210> SEQ ID NO 16
<211> LENGTH: 21
<212> TYPE: DNA
<213> ORGANISM: Artificial Sequence
<220> FEATURE:
<223> OTHER INFORMATION: blocker oligonucleotide
<220> FEATURE:
<221> NAME/KEY: misc_binding
<222> LOCATION: (21)..(21)
<223> OTHER INFORMATION: linked to a phosphate group

<400> SEQUENCE: 16
gtgagtatgt gtggtttgtg t                                           21

<210> SEQ ID NO 17
<211> LENGTH: 22
<212> TYPE: DNA
<213> ORGANISM: Artificial Sequence
<220> FEATURE:
<223> OTHER INFORMATION: blocker oligonucleotide
<220> FEATURE:
<221> NAME/KEY: misc_binding
<222> LOCATION: (22)..(22)
<223> OTHER INFORMATION: linked to a phosphate group

<400> SEQUENCE: 17
taaaccccca tcccaaatct ca                                          22

<210> SEQ ID NO 18
<211> LENGTH: 22
<212> TYPE: DNA
<213> ORGANISM: Artificial Sequence
<220> FEATURE:
<223> OTHER INFORMATION: blocker oligonucleotide
<220> FEATURE:
<221> NAME/KEY: misc_binding
<222> LOCATION: (22)..(22)
<223> OTHER INFORMATION: linked to a phosphate group

<400> SEQUENCE: 18
gtgagtatgt gtggtttgtg tt                                          22

<210> SEQ ID NO 19
<211> LENGTH: 27
<212> TYPE: DNA
<213> ORGANISM: Artificial Sequence
<220> FEATURE:
<223> OTHER INFORMATION: anchor oligonucleotide
<220> FEATURE:
<221> NAME/KEY: misc_binding
<222> LOCATION: (27)..(27)
<223> OTHER INFORMATION: linked to fluorescein

<400> SEQUENCE: 19
tttagagttt ttagtatggg gttaatt                                     27

<210> SEQ ID NO 20
<211> LENGTH: 22
<212> TYPE: DNA
<213> ORGANISM: Artificial Sequence
```

```
<220> FEATURE:
<223> OTHER INFORMATION: hybridisation probe
<220> FEATURE:
<221> NAME/KEY: misc_binding
<222> LOCATION: (1)..(1)
<223> OTHER INFORMATION: linked to "RED 705"
<220> FEATURE:
<221> NAME/KEY: misc_binding
<222> LOCATION: (22)..(22)
<223> OTHER INFORMATION: linked to a phosphate group

<400> SEQUENCE: 20
gtattaggtt tgggtttttg gt                                           22

<210> SEQ ID NO 21
<211> LENGTH: 23
<212> TYPE: DNA
<213> ORGANISM: Artificial Sequence
<220> FEATURE:
<223> OTHER INFORMATION: hybridisation probe
<220> FEATURE:
<221> NAME/KEY: misc_binding
<222> LOCATION: (1)..(1)
<223> OTHER INFORMATION: linked to "RED 650"
<220> FEATURE:
<221> NAME/KEY: misc_binding
<222> LOCATION: (23)..(23)
<223> OTHER INFORMATION: linked to a phosphate group

<400> SEQUENCE: 21
tagtattagg ttcgggtttt cgg                                          23

<210> SEQ ID NO 22
<211> LENGTH: 21
<212> TYPE: DNA
<213> ORGANISM: Artificial Sequence
<220> FEATURE:
<223> OTHER INFORMATION: primer

<400> SEQUENCE: 22
gttttctgtt attagtgagt a                                            21

<210> SEQ ID NO 23
<211> LENGTH: 21
<212> TYPE: DNA
<213> ORGANISM: Artificial Sequence
<220> FEATURE:
<223> OTHER INFORMATION: blocker oligonucleotide
<220> FEATURE:
<221> NAME/KEY: misc_binding
<222> LOCATION: (21)..(21)
<223> OTHER INFORMATION: linked to a phosphate group

<400> SEQUENCE: 23
taaaccccca tcccaaatct c                                            21

<210> SEQ ID NO 24
<211> LENGTH: 35
<212> TYPE: DNA
<213> ORGANISM: Artificial Sequence
<220> FEATURE:
<223> OTHER INFORMATION: TaqMan probe
<220> FEATURE:
<221> NAME/KEY: misc_binding
<222> LOCATION: (1)..(1)
<223> OTHER INFORMATION: linked to "Black hole"
<220> FEATURE:
<221> NAME/KEY: misc_binding
<222> LOCATION: (35)..(35)
<223> OTHER INFORMATION: linked to "FAM"
```

```
<400> SEQUENCE: 24
taattcgtag tattaggttc gggttttcgg taggg                              35

<210> SEQ ID NO 25
<211> LENGTH: 66
<212> TYPE: DNA
<213> ORGANISM: Artificial Sequence
<220> FEATURE:
<223> OTHER INFORMATION: chemically treated DNA

<400> SEQUENCE: 25
tcgtcgtcgt agttttcgtt attagtgagt acgcgcggtt cgcgttttcg gggatggggt   60
ttagag                                                             66

<210> SEQ ID NO 26
<211> LENGTH: 66
<212> TYPE: DNA
<213> ORGANISM: Artificial Sequence
<220> FEATURE:
<223> OTHER INFORMATION: chemically treated DNA

<400> SEQUENCE: 26
ttgttgttgt agtttttgtt attagtgagt atgtgtggtt tgtgtttttg gggatggggt   60
ttagag                                                             66

<210> SEQ ID NO 27
<211> LENGTH: 15
<212> TYPE: DNA
<213> ORGANISM: Artificial Sequence
<220> FEATURE:
<223> OTHER INFORMATION: primer

<400> SEQUENCE: 27
cgcgcgtact cacta                                                   15

<210> SEQ ID NO 28
<211> LENGTH: 15
<212> TYPE: DNA
<213> ORGANISM: Artificial Sequence
<220> FEATURE:
<223> OTHER INFORMATION: primer

<400> SEQUENCE: 28
crcrcrtact cacta                                                   15

<210> SEQ ID NO 29
<211> LENGTH: 15
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (2)..(2)
<223> OTHER INFORMATION: i
<220> FEATURE:
<221> NAME/KEY: misc_feature
<222> LOCATION: (4)..(4)
<223> OTHER INFORMATION: i
<220> FEATURE:
<221> NAME/KEY: misc_feature
<222> LOCATION: (6)..(6)
<223> OTHER INFORMATION: i

<400> SEQUENCE: 29
cncncntact cacta                                                   15
```

```
<210> SEQ ID NO 30
<211> LENGTH: 13
<212> TYPE: DNA
<213> ORGANISM: Artificial Sequence
<220> FEATURE:
<223> OTHER INFORMATION: primer

<400> SEQUENCE: 30
tactcactaa taa                                                        13

<210> SEQ ID NO 31
<211> LENGTH: 16
<212> TYPE: DNA
<213> ORGANISM: Artificial Sequence
<220> FEATURE:
<223> OTHER INFORMATION: blocker oligonucleotide

<400> SEQUENCE: 31
aaacacaaac cacaca                                                     16

<210> SEQ ID NO 32
<211> LENGTH: 17
<212> TYPE: DNA
<213> ORGANISM: Artificial Sequence
<220> FEATURE:
<223> OTHER INFORMATION: blocker oligonucleotide

<400> SEQUENCE: 32
aaccacacaa tgagtga                                                    17

<210> SEQ ID NO 33
<211> LENGTH: 15
<212> TYPE: DNA
<213> ORGANISM: Artificial Sequence
<220> FEATURE:
<223> OTHER INFORMATION: primer

<400> SEQUENCE: 33
crcrcrtact cacta                                                      15

<210> SEQ ID NO 34
<211> LENGTH: 18
<212> TYPE: DNA
<213> ORGANISM: Artificial Sequence
<220> FEATURE:
<223> OTHER INFORMATION: blocker oligonucleotide

<400> SEQUENCE: 34
aacgagagat actcacta                                                   18

<210> SEQ ID NO 35
<211> LENGTH: 18
<212> TYPE: DNA
<213> ORGANISM: Artificial Sequence
<220> FEATURE:
<223> OTHER INFORMATION: primer

<400> SEQUENCE: 35
aaccrcrcrt actcacta                                                   18

<210> SEQ ID NO 36
<211> LENGTH: 18
<212> TYPE: DNA
<213> ORGANISM: Artificial Sequence
<220> FEATURE:
```

-continued

```
<223> OTHER INFORMATION: blocker oligonucleotide

<400> SEQUENCE: 36
aaaaacacaa accacaca                                                    18

<210> SEQ ID NO 37
<211> LENGTH: 19
<212> TYPE: DNA
<213> ORGANISM: Artificial Sequence
<220> FEATURE:
<223> OTHER INFORMATION: blocker oligonucleotide

<400> SEQUENCE: 37
caaaaacaca aaccacaca                                                   19

<210> SEQ ID NO 38
<211> LENGTH: 13
<212> TYPE: DNA
<213> ORGANISM: Artificial Sequence
<220> FEATURE:
<223> OTHER INFORMATION: primer

<400> SEQUENCE: 38
aaaccccatc ccc                                                         13

<210> SEQ ID NO 39
<211> LENGTH: 153
<212> TYPE: DNA
<213> ORGANISM: Artificial Sequence
<220> FEATURE:
<223> OTHER INFORMATION: chemically treated DNA

<400> SEQUENCE: 39
gtttttgtta ttagtgagta tgtgtggttt gtgttttgg ggatgggtt tagagttttt         60 agtatgggt taatttgtag tattaggttt gggttttgg tagggttttt tgtttatttt       120
gagatttggg atgggggttt agggattta gga                                   153

<210> SEQ ID NO 40
<211> LENGTH: 153
<212> TYPE: DNA
<213> ORGANISM: Artificial Sequence
<220> FEATURE:
<223> OTHER INFORMATION: chemically treated DNA

<400> SEQUENCE: 40
gttttcgtta ttagtgagta cgcgcggttc gcgttttcgg ggatgggtt tagagttttt        60 agtatgggt taattcgtag tattaggttc gggttttcgg tagggttttt cgtttatttc      120
gagattcggg acgggggttt agggattta gaa                                   153
```

What is claimed is:

1. A method for the detection of cytosine methylation in DNA samples, characterized in that the following steps are conducted:
   a genomic DNA sample, which comprises the DNA to be investigated as well as background DNA, is chemically treated in such a way that all unmethylated cytosine bases are converted to uracil, while 5-methylcytosine bases remain unchanged;
   the chemically treated DNA sample is amplified with the use of at least 2 primer oligonucleotides, as well as a polymerase and at least one blocking oligonucleotide or PNA oligomer which preferentially binds to a 5'-CG-3' dinucleotide or a 5'-TG-3' dinucleotide or a 5'-CA-3' dinucleotide on the background DNA, whereby the DNA to be investigated is preferentially amplified over the background DNA as the template, and
   the amplified products are analyzed and the methylation status in the DNA to be investigated is concluded from the presence of an amplified product and/or from the analysis of the amplified product.

2. The method according to claim 1, further characterized in that the sample DNA is obtained from serum or other body fluids of an individual.

3. The method according to claim 1, further characterized in that the DNA samples are obtained from cell lines, blood, sputum, stool, urine, serum, cerebro-spinal fluid, tissue embedded in paraffin, said tissue being selected from the group consisting of eyes, intestine, kidneys, brain, heart, prostate, lungs, breast and liver, histological slides and any combination thereof.

4. The method according to claim 1, further characterized in that the chemical treatment is conducted with a bisulfite.

5. The method according to claim 4, further characterized in that the chemical treatment is conducted after embedding the DNA in agarose.

6. The method according to claim 4, further characterized in that a reagent denaturing the DNA duplex and/or a radical trap is present in the chemical treatment.

7. The method according to claim 1, characterized in that at least one of the at least two primer oligonucleotides in the amplification step preferentially binds to the DNA to be investigated over the background DNA.

8. The method according to claim 1, further characterized in that the blocking oligonucleotide or PNA oligomer binds to the background DNA at a site that overlaps where the primer oligonucleotides bind to the background DNA, thereby hindering binding of at least one of the primer oligonucleotides to the background DNA.

9. The method according to claim 1, further characterized in that at least two blocking oligonucleotides or PNA oligomers are utilized, wherein said at least two blocking olignucleotides or PNA oligomers bind to the background DNA at one or more sites that overlap where both primer oligonucleotides bind to the background DNA.

10. The method according to claim 9, further characterized in that one of the blocking oligonucleotides and/or PNA oligomers hinders the binding of the forward primer, while the other one hinders the binding of the reverse primer.

11. The method according to claim 1, further characterized in that the blocking oligonucleotides and/or PNA oligomers are present in at least five times the concentration in comparison to the primer oligonucleotides.

12. The method according to claim 1, further characterized in that the blocking oligonucleotides and/or PNA oligomers bind to the background DNA and thus hinder the complete elongation of primer oligonucleotides in the polymerase reaction.

13. The method according to claim 12, further characterized in that the polymerase used has no 5'-3' exonuclease activity.

14. The method according to claim 12, further characterized in that the blocking oligonucleotides are modified at the 5' end and thus cannot be broken down by a polymerase with 5'-3' exonuclease activity.

15. The method according to claim 1, further characterized in that the blocking oligonucleotides that are used in addition to the primers do not make available a 3'-OH functional group.

16. The method according to claim 1, further characterized in that the blocking oligonucleotide or PNA oligomer hybridizes to a 5'-CG-3' dinucleotide or a 5'-TG-3' dinucleotide or a 5'-CA-3' dinucleotide, said amplification further including the use of at least one reporter oligonucleotide which hybridizes to a 5'-CG-3' dinucleotide or a 5'-TG-3' dinucleotide or a 5'-CA-3' dinucleotide, whereby the blocking oligonucleotide or PNA oligomer preferentially binds to the background DNA over the DNA to be investigated and minimizes its amplification, and whereby the reporter oligonucleotide preferentially binds to the DNA to be investigated over the background DNA and indicates its amplification.

17. The method according to claim 16, further characterized in that in addition to the reporter nucleotide, another oligomer labeled with a fluorescent dye is used, which hybridizes directly adjacent to the reporter oligonucleotide and this hybridization can be detected by means of fluorescence resonance energy transfer.

18. The method according to claim 16, further characterized in that the reporter oligonucleotides bear at least one fluorescent label.

19. The method according to claim 16, further characterized in that the reporter molecules indicate the amplification either by an increase or a decrease in the fluorescence.

20. The method according to claim 19, further characterized in that the increase or decrease in the fluorescence is also used directly for the analysis and a methylation state of the DNA to be analyzed is concluded from the fluorescent signal.

21. The method according to claim 1, further characterized in that the background DNA is present in 100 times the concentration of the DNA to be investigated.

22. The method according to claim 1, further characterized in that the background DNA is present in 1000 times the concentration of the DNA to be investigated.

23. The method according to claim 1, further characterized in that the analysis is conducted by means of hybridization to oligomer arrays, wherein oligomers can be nucleic acids or PNAs.

24. The method according to claim 23, further characterized in that the oligomers hybridize to the DNA to be analyzed over a 12-22 base long segment and they contain a CG, TG or CA dinucleotide.

25. The method according to claim 23, further characterized in that the methylation status of more than 20 methylation positions of the DNA to be analyzed is detected in one experiment.

26. The method according to claim 23, further characterized in that the methylation status of more than 60 methylation positions of the DNA to be analyzed is detected in one experiment.

27. The method according to claim 1, further characterized in that the analysis is conducted by length measurement of the amplified DNA to be investigated, whereby methods for length measurement include gel electrophoresis, capillary gel electrophoresis, chromatography, and mass spectrometry.

28. The method according to claim 1, further characterized in that the analysis is conducted by sequencing.

29. The method according to claim 28, further characterized in that the sequencing is conducted for each CpG position or a group of these positions with a separate primer oligonucleotide and the elongation of the primer is by no more than a few bases, and the methylation status of the respective positions in the DNA to be investigated is concluded from the type of primer extension.

30. The method according to claim 1, further characterized in that the presence of a disease or adverse medical condition of the patient is concluded.

31. The method according to claim 1, further characterized in that the amplified products themselves are provided with a detectable label for detection.

32. The method according to claim 31, further characterized in that the labels are fluorescent labels.

33. The method according to claim 31, further characterized in that the labels are radionuclides.

34. The method according to claim 31, further characterized in that the labels are removable mass labels, which are detected in a mass spectrometer.

35. The method according to claim 1, further characterized in that one of the primers is bound to a solid phase in the amplification.

36. The method according to claim 1, further characterized in that the amplified products are detected as a whole in the mass spectrometer and are thus characterized by their mass.

37. Use of a method according to claim 1 for the diagnosis and/or prognosis of adverse events for patients or individuals, wherein these adverse events belong to at least one of the following categories: drug interactions; cancer diseases; CNS malfunctions, damage or disease; symptoms of aggression or behavioral disturbances; clinical, psychological and social consequences of brain damage; psychotic disturbances and personality disorders; dementia and/or associated syndromes; cardiovascular disease, malfunction and damage; malfunction, damage or disease of the gastrointestinal tract; malfunction, damage or disease of the respiratory system; lesion, inflammation, infection, immunity and/or convalescence; malfunction, damage or disease of the body as an abnormality in the development process; malfunction, damage or disease of the skin, the muscles, the connective tissue or the bones; endocrine and metabolic malfunction, damage or disease; headaches or sexual malfunction.

38. The use of a method according to claim 1 for distinguishing cell types or tissues or for investigating cell differentiation.

39. A kit for conducting an assay according to any one of claims 1-6, 7-17 or 18-36, comprised of a reagent containing bisulfite, primers and at least one blocking oligonucleotide or PNA oligomer which preferentially binds to a 5'-CG-3' dinucleotide or a 5'-TG-3' dinucleotide or a 5'-CA-3' dinucleotide on the background DNA relative to the template DNA, and, optionally, directions for conducting said assay.

* * * * *